United States Patent
Lee et al.

(10) Patent No.: US 7,894,908 B2
(45) Date of Patent: Feb. 22, 2011

(54) NEUROSTIMULATION THERAPY OPTIMIZATION BASED ON A RATED SESSION LOG

(75) Inventors: Michael T. Lee, Minnetonka, MN (US); Daniel K. Vinup, Maple Grove, MN (US); Steven M. Goetz, Brooklyn Center, MN (US)

(73) Assignee: Medtronic, Inc., Minneapolis, MN (US)

( * ) Notice: Subject to any disclaimer, the term of this patent is extended or adjusted under 35 U.S.C. 154(b) by 1219 days.

(21) Appl. No.: 10/406,039

(22) Filed: Apr. 2, 2003

(65) Prior Publication Data

US 2004/0199216 A1 Oct. 7, 2004

(51) Int. Cl.
*A61N 1/365* (2006.01)

(52) U.S. Cl. .................................................. 607/48

(58) Field of Classification Search ................ 600/373, 600/377, 378, 544; 607/1, 2, 30, 32, 46, 607/59, 60, 117, 118, 133
See application file for complete search history.

(56) References Cited

U.S. PATENT DOCUMENTS

| | | | |
|---|---|---|---|
| 4,515,158 A | | 5/1985 | Patrick et al. |
| 4,520,825 A | | 6/1985 | Thompson et al. |
| 4,549,548 A | | 10/1985 | Wittkampf et al. |
| 4,793,353 A | * | 12/1988 | Borkan ........................ 607/60 |
| 4,958,632 A | | 9/1990 | Duggan |
| 5,033,469 A | | 7/1991 | Brodard |
| 5,159,926 A | | 11/1992 | Ljungstroem |
| 5,300,096 A | | 4/1994 | Hall et al. |
| 5,350,414 A | | 9/1994 | Kolen |
| 5,370,672 A | * | 12/1994 | Fowler et al. .................. 607/58 |
| 5,443,486 A | | 8/1995 | Hrdlicka et al. |
| 5,653,739 A | | 8/1997 | Maurer et al. |
| 5,716,384 A | | 2/1998 | Snell |

(Continued)

FOREIGN PATENT DOCUMENTS

EP 0 730 882 9/1996

(Continued)

OTHER PUBLICATIONS

International Search Report for PCT/US2004/002182, filed Jan. 27, 2004.

(Continued)

*Primary Examiner*—Carl H Layno
*Assistant Examiner*—Frances P Oropeza
(74) *Attorney, Agent, or Firm*—Shumaker & Sieffert, P.A.

(57) ABSTRACT

An implantable medical device (IMD) delivers neurostimulation therapy to a patient according to a parameter set, which may consist of a number of programs that are delivered substantially simultaneously. When programming the IMD, a clinician programmer may maintain a session log for the patient that includes a listing of programs delivered to the patient and rating information provided by a clinician and the patient for programs of the list. The listing may be ordered according to the rating information in order to facilitate the selection of programs for a parameter set. A program library that may include particularly effective programs organized according to a directory structure may be stored in a memory. The IMD and/or a patient programmer may store usage information that provides an objective assessment of therapy use by the patient, and allows a clinician to later improve the therapy based on the usage information.

56 Claims, 18 Drawing Sheets

U.S. PATENT DOCUMENTS

| | | | |
|---|---|---|---|
| 5,722,999 | A | 3/1998 | Snell |
| 5,755,736 | A | 5/1998 | Gillberg et al. |
| 5,755,745 | A | 5/1998 | McGraw et al. |
| 5,775,331 | A | 7/1998 | Raymond et al. |
| 5,776,171 | A | 7/1998 | Peckham et al. |
| 5,776,173 | A | 7/1998 | Madsen, Jr. et al. |
| 5,807,397 | A | 9/1998 | Barreras |
| 5,843,142 | A | 12/1998 | Sultan |
| 5,891,178 | A | 4/1999 | Mann et al. |
| 5,893,883 | A | 4/1999 | Torgerson et al. |
| 5,938,690 | A | 8/1999 | Law et al. |
| 6,044,303 | A | 3/2000 | Agarwala et al. |
| 6,052,624 | A | 4/2000 | Mann |
| 6,120,467 | A | 9/2000 | Schallhorn |
| 6,175,764 | B1 | 1/2001 | Loeb et al. |
| 6,205,359 | B1 | 3/2001 | Boveja |
| 6,249,703 | B1 | 6/2001 | Stanton et al. |
| 6,308,100 | B1 | 10/2001 | Er et al. |
| 6,308,102 | B1 | 10/2001 | Sieracki et al. |
| 6,321,117 | B1 | 11/2001 | Koshiol et al. |
| 6,381,496 | B1 | 4/2002 | Meadows et al. |
| 6,393,325 | B1 | 5/2002 | Mann et al. |
| 6,440,090 | B1 | 8/2002 | Schallhorn |
| 6,463,328 | B1 * | 10/2002 | John ........................ 607/45 |
| 6,473,653 | B1 | 10/2002 | Schallhorn et al. |
| 6,480,743 | B1 | 11/2002 | Kirkpatrick et al. |
| 6,516,227 | B1 | 2/2003 | Meadows et al. |
| 6,564,807 | B1 | 5/2003 | Schulman et al. |
| 6,587,724 | B2 | 7/2003 | Mann |
| 6,609,032 | B1 | 8/2003 | Woods et al. |
| 6,654,642 | B2 * | 11/2003 | North et al. ................. 607/59 |
| 2002/0107553 | A1 | 8/2002 | Hill et al. |
| 2002/0116036 | A1 | 8/2002 | Daignault, Jr. et al. |
| 2002/0169484 | A1 | 11/2002 | Mathis et al. |
| 2003/0004549 | A1 | 1/2003 | Hill et al. |
| 2003/0028223 | A1 | 2/2003 | Olson |
| 2003/0036783 | A1 | 2/2003 | Bauhahn et al. |
| 2004/0111131 | A1 | 6/2004 | Hu et al. |
| 2004/0143302 | A1 * | 7/2004 | Sieracki et al. ............. 607/48 |
| 2004/0158298 | A1 | 8/2004 | Gliner et al. |
| 2005/0177206 | A1 * | 8/2005 | North et al. ................. 607/60 |
| 2005/0209655 | A1 * | 9/2005 | Bradley et al. ............. 607/48 |
| 2005/0283210 | A1 | 12/2005 | Blischak et al. |

FOREIGN PATENT DOCUMENTS

| | | |
|---|---|---|
| EP | 1 249 254 | 10/2002 |
| EP | 1304137 | 4/2003 |
| WO | WO 97/43002 | 11/1997 |
| WO | WO 98/29160 | 7/1998 |
| WO | WO 01/93953 | 12/2001 |
| WO | WO 02/09808 | 2/2002 |
| WO | WO 2004/041352 | 5/2004 |
| WO | WO2006/012423 | 2/2006 |

OTHER PUBLICATIONS

Notification of Transmittal of the International Preliminary Report on Patentability for PCT/US2004/002182, filed Jan. 27, 2004.

Robin et al., "A New Implantable Microstimulator Dedicated to Selective Stimulation of the Bladder," Proceedings—19th International Conference—IEEE/EMBS Oct. 30-Nov. 2, 1997, Chigaco, IL, pp. 1792-1795.

"GenesisXP™ Neurostimulation Systems," Implantable Therapies for Chronic Pain and Neurological Disorders, http://www.ans medical.com/physicians/GenesisXPSystem/XPOverview.cfm.

"PainDoc® Computerized Support System," Implantable Therapies for Chronic Pain and Neurological Disorders, http://www.ans-medical.com/physicians/PainDoc/PainDoc.html.

"MultiStim®," Implantable Therapies for Chronic Pain and Neurological Disorders, http://www.ans medical.com/physicians/RenewRFSystem/MultiStim.html.

"PC-Stim®," Implantable Therapies for Chronic Pain and Neurological Disorders, http://www.ans medical.com/physicians/RenewRFSystem/PCStim.html.

"Renew® Neurostimulation System Overview," Implantable Therapies for Chronic Pain and Neurological Disorders, http://www.ans-medical.com/physicians/RenewRFSystem/SystemOverview.html.

U.S. Appl. No. 10/406,038, filed Apr. 2, 2003, titled "Neurostimulation Therapy Usage Diagnostics."

U.S. Appl. No. 10/406,040, filed Apr. 2, 2003, titled "Management of Neurostimulation Therapy Using Parameter Sets."

U.S. Appl. No. 10/406,041, filed Apr. 2, 2003, titled "Library for Management of Neurostimulation Therapy Programs."

Office Action dated May 2, 2008 for U.S. Appl. No. 10/406,041 (10 pgs.).

Responsive Amendment dated Aug. 4, 2008 for U.S. Appl. No. 10/406,041 (19 pgs.).

Office Action dated Jul. 24, 2008 for U.S. Appl. No. 11/388,227 (10 pgs.).

Office Action dated Apr. 29, 2008 for U.S. Appl. No. 11/186,383 (11 pgs.).

Responsive Amendment dated Aug. 29, 2008 for U.S. Appl. No. 11/186,383 (19 pgs.).

Responsive Amendment dated Oct. 24, 2008 for U.S. Appl. No. 11/388,227 (18 pgs.).

Office Action for U.S. Appl. No. 11/186,383, mailed Jan. 7, 2009, 17 pages.

Amendment to Office Action for U.S. Appl. No. 11/186,383, filed Apr. 7, 2009, 25 pages.

Office Action for U.S. Appl. No. 11/388,227, mailed Jan. 22, 2009, 13 pages.

Amendment to Office Action for U.S. Appl. No. 11/388,227, filed Apr. 22, 2009, 19 pages.

Office Action for U.S. Appl. No. 11/186,383, mailed May 7, 2009, 13 pages.

Amendment to Office Action for U.S. Appl. No. 11/186,383, filed Aug. 7, 2009, 29 pages.

Office Action for U.S. Appl. No. 11/388,227, mailed Aug. 17, 2009, 11 pages.

Responsive Amendment for U.S. Appl. No. 11/388,227, filed Nov. 13, 2009, 23 pages.

Office Action dated Jul. 18, 2008 for U.S. Appl. No. 10/406,038, (10 pgs.).

Responsive Amendment dated Sep. 18, 2008 for U.S. Appl. No. 10/406,038 (8 pgs.).

Office Action for U.S. Appl. No. 11/388,227, mailed Jan. 29, 2010, 8 pages.

Response to Office Action for U.S. Appl. No. 11/388,227, filed Apr. 28, 2010, 12 pages.

Request for Continued Examination (RCE), Response to Final Office Action and Advisory Action, for U.S. Appl. No. 11/186,383, filed Jul. 28, 2010, 27 pages.

Final Office Action for U.S. Appl. No. 11/186,383, mailed Mar. 29, 2010, 15 pages.

Response to Final Office Action for U.S. Appl. No. 11/186,383, filed May 27, 2010, 20 pages.

Advisory Action for U.S. Appl. No. 11/186,383, mailed Jun. 14, 2010, 3 pages.

Office Action for U.S. Appl. No. 12/498,645, mailed Sep. 14, 2010, 8 pages.

Responsive Amendment to Office Action for U.S. Appl. No. 12/498,645, filed Nov. 29, 2010, 14 pages.

* cited by examiner

NEUROSTIMULATION THERAPY OPTIMIZATION BASED ON A RATED SESSION LOG

TECHNICAL FIELD

The invention relates to neurostimulation therapy and, more particularly, to management of information relating to neurostimulation therapy and delivery of neurostimulation therapy.

BACKGROUND

Implantable medical devices may be used to deliver neurostimulation therapy to patients to treat a variety of symptoms or conditions such as chronic pain, tremor, Parkinson's disease, epilepsy, incontinence, or gastroparesis. An implantable medical device may deliver neurostimulation therapy via leads that include electrodes located proximate to the spinal cord, pelvic nerves, or stomach, or within the brain of a patient. In general, the implantable medical device delivers neurostimulation therapy in the form of electrical pulses.

A clinician may select values for a number of programmable parameters in order to define the neurostimulation therapy to be delivered to a patient. For example, the clinician may select a voltage or current amplitude and pulse width for a stimulation waveform to be delivered to the patient, as well as a rate at which the pulses are to be delivered to the patient. The clinician may also select as parameters particular electrodes within an electrode set to be used to deliver the pulses, and the polarities of the selected electrodes. A group of parameter values may be referred to as a program in the sense that they drive the neurostimulation therapy to be delivered to the patient.

The process of selecting values for the parameters that provide adequate results can be time consuming, and may require a great deal of trial and error before a "best" program, e.g., a program that is better in terms of clinic efficacy versus side effects experienced than other programs tested, is discovered. The clinician may be required to make notations describing a number of programs and feedback received from the patient regarding the perceived efficacy of each program. The clinician may then select the "best" program based on the notations.

Even after this often-lengthy process, the selected program may be inadequate to alleviate all of the symptoms of the patient. The symptoms may vary throughout the day or depending on the position of the patient, e.g., standing, sitting, lying down, etc. Additionally, the symptoms may change over a longer period of time such that the selected program is no longer effective, often requiring the clinician to start the program selection process anew.

SUMMARY

In general, the invention is directed to techniques for management of information relating to neurostimulation therapy and delivery of neurostimulation therapy. An implantable medical device delivers neurostimulation therapy to a patient according to a parameter set. A parameter set contains one or more programs that can be delivered to the patient. Each program includes a group of parameter values. The one or more programs of a parameter set may be delivered to the patient substantially simultaneously. For example, each pulse may deliver neurostimulation therapy according to a different program. In this manner, multiple programs may be delivered, e.g., to treat multiple symptoms.

A clinician programs neurostimulation therapy for the patient using a clinician programmer. The clinician specifies programs to treat various symptoms of the patient, and groups some of the specified programs into a parameter set. In accordance with the invention, multiple parameter sets may be created, and the parameter sets may be transmitted to one or both of the implantable medical device and a patient programmer.

The clinician may specify a program using the clinician programmer by selecting values for various program parameters, such as pulse amplitude, pulse width, and pulse rate, and by selecting which of the electrodes of the electrode set implanted within the patient will deliver pulses, and polarities of selected electrodes. When a program is specified, the clinician may test the program on the patient by directing the clinician programmer to control the implantable medical device to deliver neurostimulation therapy. In particular, the clinician programmer may transmit the program to the implantable medical device so that the implantable medical device delivers neurostimulation therapy according to the transmitted program. The clinician may receive feedback from the patient regarding the perceived effectiveness and side effects associated with the delivered program.

While the clinician is programming the implantable medical device for the patient, the clinician programmer may maintain a session log for the patient that includes a listing of programs tested on the patient and rating information provided by the clinician and the patient for programs of the list. The rating information may be entered by the clinician using the clinician programmer, and may include information relating to effectiveness of delivery of neurostimulation therapy according to the program in treating symptoms of the patient, side effects experienced by the patient due to the delivery of neurostimulation therapy according to the program, or both. The listing may be ordered according to the rating information in order to facilitate the selection of programs from the list for a parameter set by the clinician. The session log for the patient may be stored in a non-volatile medium or database for future reference by the clinician, and may be updated by the clinician during follow-up visits by the patient.

In one embodiment, the invention is directed to a method comprising controlling an implantable medical device to deliver neurostimulation therapy to a patient according to a neurostimulation therapy program, recording rating information relating to effectiveness of delivery of neurostimulation therapy according to the program in treating symptoms of the patient and side effects experienced by the patient due to the delivery of neurostimulation therapy according to the program in response to the delivery, and associating the program and the rating information in a memory.

In another embodiment, the invention is directed to a device comprising a memory to store information, and a processor to control an implantable medical device to deliver neurostimulation therapy to a patient according to a neurostimulation therapy program, record rating information relating to effectiveness of delivery of neurostimulation therapy according to the program in treating symptoms of the patient and side effects experienced by the patient due to the delivery of neurostimulation therapy according to the program in response to the delivery, and associate the program and the rating information in the memory.

In an added embodiment, the invention is directed to a computer-readable medium, comprising instructions that cause a processor to control an implantable medical device to deliver neurostimulation therapy to a patient according to a neurostimulation therapy program, and record rating information relating to effectiveness of delivery of neurostimulation therapy according to the program in treating symptoms of the patient and side effects experienced by the patient due to the delivery of neurostimulation therapy according to the program in response to the delivery, and associate the program and the rating information in a memory.

In a further embodiment, the invention provides a method comprising storing information identifying neurostimulation therapy programs tested on a patient during a programming session and rating information associated with each of the neurostimulation therapy programs that relates to effectiveness of delivery of neurostimulation therapy according to the programs in treating symptoms of the patient and side effects experienced by the patient due to the delivery of neurostimulation therapy according to the programs in a memory as part of a session log for programming session, and displaying a list of the identified programs and associated rating information via a display.

In another embodiment, the invention provides a device comprising a display to display information to a user, a memory to store a session log for a patient that includes information identifying neurostimulation therapy programs tested on the patient during a programming session and rating information associated with each of the neurostimulation therapy programs that relates to effectiveness of delivery of neurostimulation therapy according to the programs in treating symptoms of the patient and side effects experienced by the patient due to the delivery of neurostimulation therapy according to the programs, and a processor to display a list of the identified programs and associated rating information via the display.

In an added embodiment, the invention provides a computer-readable medium comprising instructions that cause a processor to store a session log for a patient that includes information identifying neurostimulation therapy programs tested on the patient during a programming session and rating information associated with each of the neurostimulation therapy programs that relates to effectiveness of delivery of neurostimulation therapy according to the programs in treating symptoms of the patient and side effects experienced by the patient due to the delivery of neurostimulation therapy according to the programs in a memory, and display a list of the identified programs and associated rating information via a display.

The invention may provide a number of advantages. For example, by maintaining a session log during programming of neurostimulation therapy for the patient, a clinician programmer may allow the clinician to more easily and quickly identify which of the programs tested on the patient to include in parameter sets that will be used for delivery of neurostimulation therapy to the patient. The clinician may use the clinician programmer to record feedback received from the patient regarding tested programs as rating information. The tested programs may be listed, and the list may include the rating information.

The list may be ordered according to the rating information to allow the clinician to more quickly identify preferred programs. In some embodiments, the rating information may relate to a number of metrics for evaluating neurostimulation therapy, and the list may be ordered according to a metric selected by the clinician. The session log also facilitates redelivery and comparison of listed programs in order to, for example, select between programs with similar ratings. The session log allows the clinician to determine which programs are preferred without relying on human memory or handwritten notes.

Storing the session log for the patient in a non-volatile medium or database may allow the clinician to more easily update the neurostimulation therapy for the patient at a follow-up visit in the event that the symptoms of the patient or their severity changes. The ratings of programs may be updated over time, and a record of the neurostimulation therapy provided to the patient may be maintained. The session log may be used as proof of the extent of the service provided by the clinician for reimbursement, or the quality of the services in the event of malpractice accusations.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
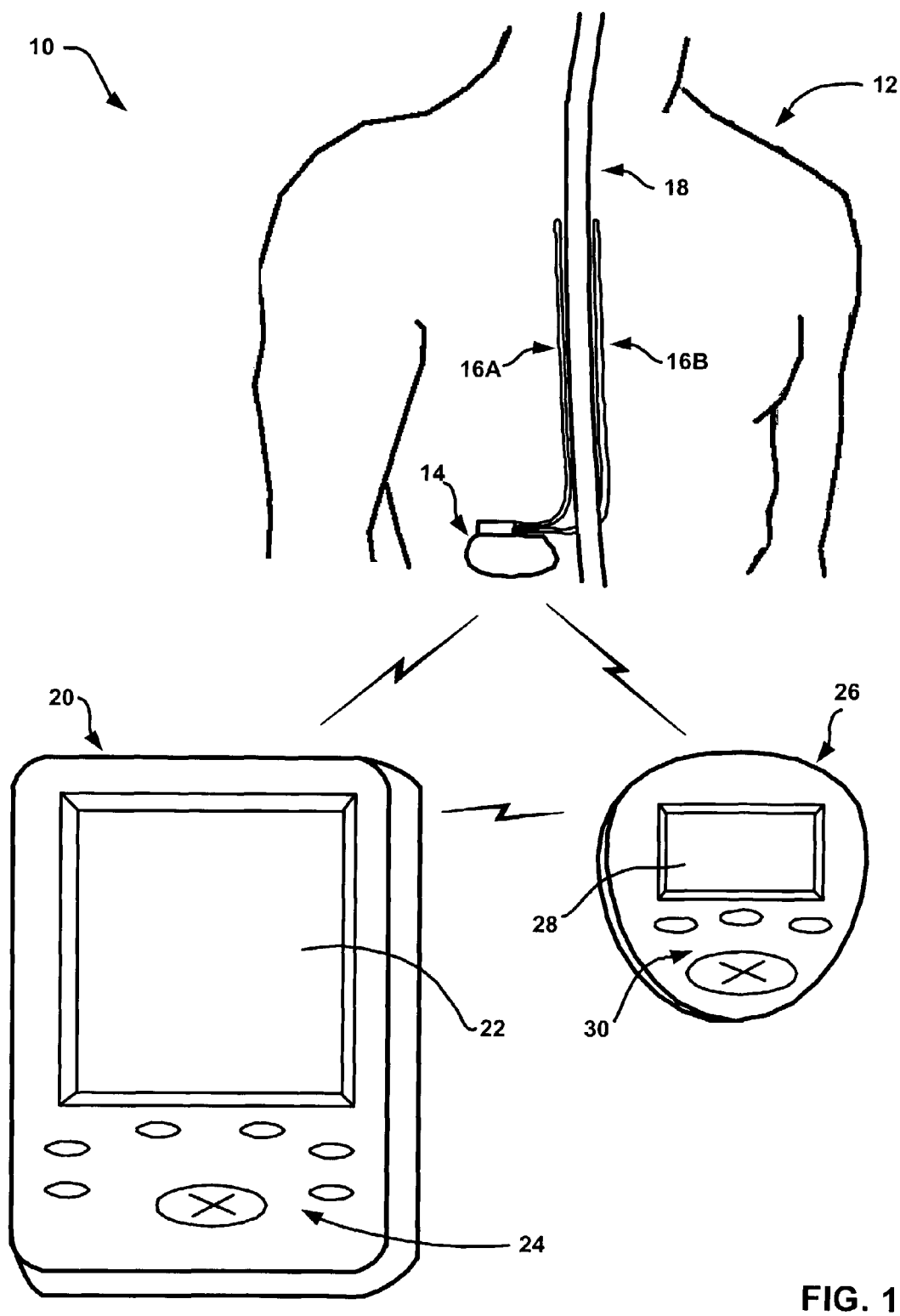
FIG. 1 is a diagram illustrating an example system for managing delivery of neurostimulation therapy to a patient and information relating to neurostimulation therapy according to the invention.

FIG. 1 is a diagram illustrating an example system 10 for managing delivery of neurostimulation therapy to a patient 12 and information relating to neurostimulation therapy according to the invention. System 10 includes an implantable medical device 14 that delivers neurostimulation therapy to patient 12. IMD 14 may be an implantable pulse generator, and may deliver neurostimulation therapy to patient 12 in the form of electrical pulses.

IMD 14 delivers neurostimulation therapy to patient 12 via leads 16A and 16B (collectively "leads 16"). Leads 16 may, as shown in FIG. 1, be implanted proximate to the spinal cord 18 of patient 12, and IMD 14 may deliver spinal cord stimulation (SCS) therapy to patient 12 in order to, for example, reduce pain experienced by patient 12. However, the invention is not limited to the configuration of leads 16 shown in FIG. 1 or the delivery of SCS therapy. For example, one or more leads 16 may extend from IMD 14 to the brain (not shown) of patient 12, and IMD 14 may deliver deep brain stimulation (DBS) therapy to patient 12 to, for example, treat tremor or epilepsy. As further examples, one or more leads 16 may be implanted proximate to the pelvic nerves (not shown) or stomach (not shown), and IMD 14 may deliver neurostimulation therapy to treat incontinence or gastroparesis.

IMD 14 delivers neurostimulation therapy according to parameter sets. A parameter set includes at least one neurostimulation therapy program. Each program may include values for a number of parameters, and the parameter values define the neurostimulation therapy delivered according to that program. In embodiments where IMD 14 delivers neurostimulation therapy in the form of electrical pulses, the parameters may include voltage or current pulse amplitudes, pulse widths, pulse rates, and the like. Further, each of leads 16 includes electrodes (not shown in FIG. 1), and the parameters for a program may include information identifying which electrodes have been selected for delivery of pulses according to the program, and the polarities of the selected electrodes.

Each program of a parameter set may be designed to address a particular symptom of patient 12. For example, in the case of SCS, each program may be designed to reduce the pain experienced by patient 12 in a different location of the body of patient 12. Further, IMD 14 may deliver neurostimulation therapy according to multiple programs of a parameter set at substantially the same time. For example, in embodiments where IMD 14 delivers neurostimulation therapy as electrical pulses, each pulse may be delivered according to a different program of the parameter set. Thus, a series of n pulses may deliver therapy according to n different programs. Delivery of neurostimulation therapy according to parameter sets may allow IMD 14 to address the symptoms of patient 12 more completely than if single program therapies were delivered. Moreover, substantially simultaneous delivery of the programs of a parameter set may make the delivery of neurostimulation therapy more comfortable for patient 12 to the extent that it prevents patient 12 from sensing program changes.

System 10 also includes a clinician programmer 20. Clinician programmer 20 may, as shown in FIG. 1, be a handheld computing device. Clinician programmer 20 includes a display 22, such as a LCD or LED display, to display information to a user. Clinician programmer 20 may also include a keypad 24, which may be used by a user to interact with clinician programmer 20. In some embodiments, display 22 may be a touch screen display, and a user may interact with clinician programmer 20 via display 22. A user may also interact with clinician programmer 20 using peripheral pointing devices, such as a stylus or mouse. Keypad 24 may take the form of an alphanumeric keypad or a reduced set of keys associated with particular functions.

A clinician (not shown) may use clinician programmer 20 to program neurostimulation therapy for patient 12. As will be described in greater detail below, the clinician may select existing programs or specify programs by selecting program parameter values, and test the selected or specified programs on patient 12. The clinician may receive feedback from patient 12, and store information identifying the programs and rating information associated with the programs as a session log for patient 12. The clinician may use the session log to more quickly select effective programs to be included in parameter sets for delivery of neurostimulation therapy for patient 12.

System 10 also includes a patient programmer 26, which also may, as shown in FIG. 1, be a handheld computing device. Patient programmer 26 may also include a display 28 and a keypad 30, to allow patient 12 to interact with patient programmer 26. In some embodiments, display 26 may be a touch screen display, and patient 12 may interact with patient programmer 26 via display 28. Patient 12 may also interact with patient programmer 26 using peripheral pointing devices, such as a stylus or mouse.

Patient 12 may use patient programmer 26 to control the delivery of neurostimulation therapy by IMD 14. Patient 12 may use patient programmer 26 to activate or deactivate neurostimulation therapy and, as will be described in greater detail below, may use patient programmer 26 to select the parameter set that will be used by IMD 14 to deliver neurostimulation therapy from one or more lists of parameter sets. Further, patient 12 may use patient programmer 26 to make adjustments to parameter sets, as will be described in greater detail below.

Allowing patient 12 greater control over the delivery of neurostimulation therapy within limits set by the clinician using patient programmer 26 may lead to more effective therapy and efficient use of clinician time. Patient 12 may be able to select parameter sets and make adjustments in order to address changes in symptoms, which may occur throughout the day, or based on changes in the position, posture, or activity of the patient. These modifications and improvements to neurostimulation therapy may occur without clinician intervention. Further, the clinician may be able to spend less time initially programming neurostimulation therapy for patient 12 by providing a variety of parameter sets at implant from which patient 12 may choose, allowing patient 12 to experiment with the parameter sets, and optimize, improve, or tailor the neurostimulation therapy over time.

Parameter sets programmed by the clinician using clinician programmer 20 may be transmitted to and stored within one or both of patient programmer 26 and IMD 14. Where the parameter sets are stored in patient programmer 26, patient programmer 26 may transmit the parameter set selected by patient 12 to IMD 14 for delivery of neurostimulation therapy to patient 12 according to the selected parameter set. Where the parameter sets are stored in IMD 14, patient programmer 26 may receive a list of parameter sets from IMD 14 to display to patient 12, and transmit an indication of the selected parameter set to IMD 14 for delivery of neurostimulation therapy to patient 12 according to the selected parameter set.

IMD 14, clinician programmer 20 and patient programmer 26 may, as shown in FIG. 1, communicate via wireless communication. Clinician programmer 20 and patient programmer 26 may, for example, communicate via wireless communication with IMD 14 using RF telemetry techniques known in the art. Clinician programmer 20 and patient programmer 26 may communicate with each other using any of a variety of local wireless communication techniques, such as RF communication according to the 802.11 or Bluetooth specification sets, infrared communication according to the IRDA specification set, or other standard or proprietary telemetry protocols. Clinician programmer 20 and patient programmer 26 need not communicate wirelessly, however. For example, programmers 20 and 26 may communicate via a wired connection, such as via a serial communication cable, or via exchange of removable media, such as magnetic or optical disks, or memory cards or sticks. Further, clinician programmer 20 may communicate with one or both of IMD 14 and patient programmer 26 via remote telemetry techniques known in the art, communicating via a local area network (LAN), wide area network (WAN), public switched telephone network (PSTN), or cellular telephone network, for example.

Figure 2:
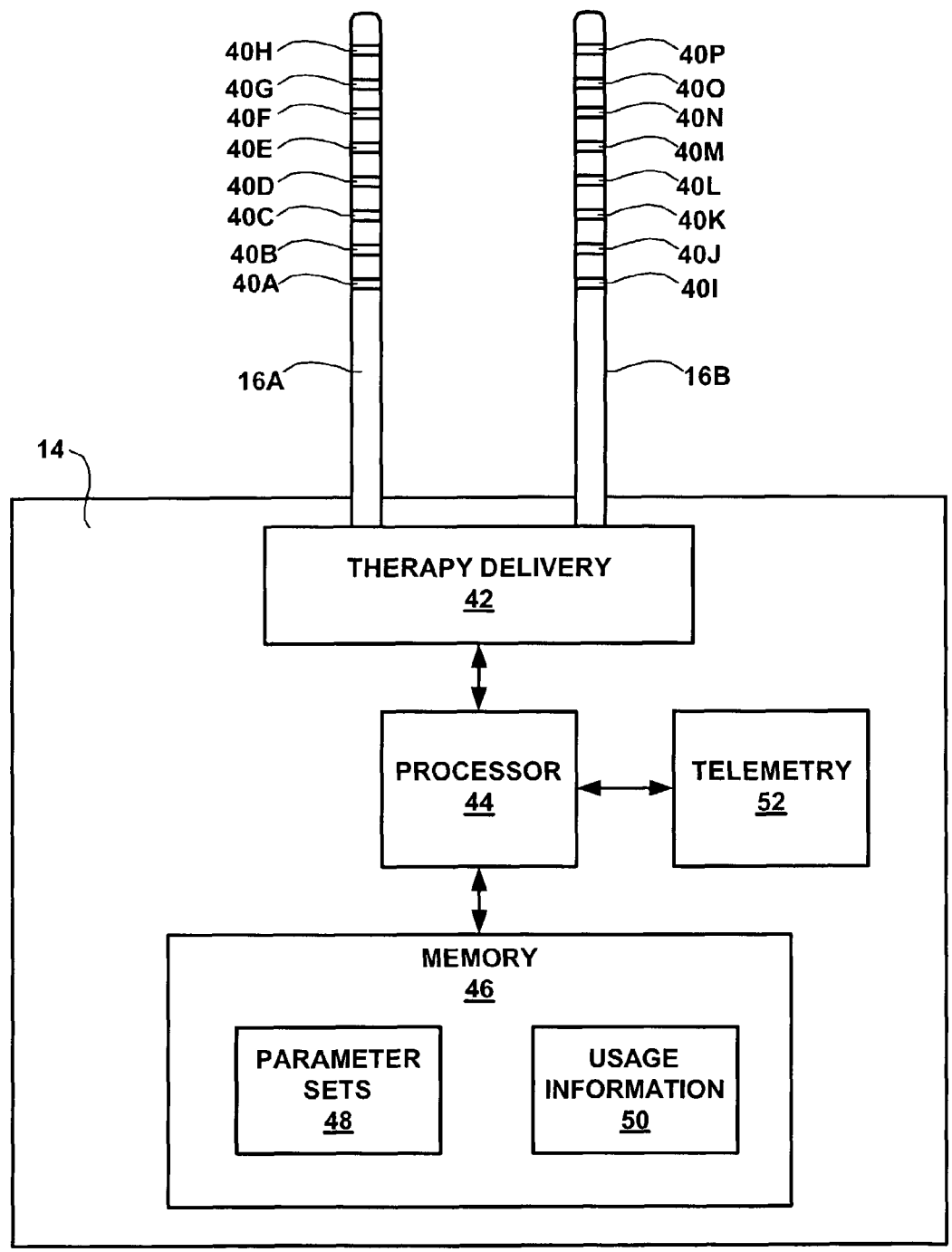
FIG. 2 is a block diagram illustrating an example implantable medical device for delivering neurostimulation therapy to a patient according to a parameter set and collecting neurostimulation therapy usage information.

FIG. 2 is a block diagram illustrating an example configuration of IMD 14. IMD 14 may deliver neurostimulation therapy via electrodes 40A-H of lead 16A and electrodes 40I-P of lead 16B (collectively "electrodes 40"). Electrodes 40 may be ring electrodes. The configuration, type and number of electrodes 40 illustrated in FIG. 2 are merely exemplary.

Electrodes 40 are electrically coupled to a therapy delivery circuit 42 via leads 16. Therapy delivery circuit 42 may, for example, include an output pulse generator coupled to a power source such as a battery. Therapy delivery circuit 42 may deliver electrical pulses to patient 12 via at least some of electrodes 40 under the control of a processor 44.

Processor 44 controls therapy delivery circuit 42 to deliver neurostimulation therapy according to a selected parameter set. Specifically, processor 44 may control circuit 42 to deliver electrical pulses with the amplitudes and widths, and at the rates specified by the programs of the selected parameter set. Processor 44 may also control circuit 42 to deliver the pulses via a selected subset of electrodes 40 with selected polarities, as specified by the programs of the selected parameter set. Processor 44 may control circuit 42 to deliver each pulse according to a different program of the parameter set. Processor 44 may include a microprocessor, a controller, a DSP, an ASIC, an FPGA, discrete logic circuitry, or the like.

IMD 14 also includes a memory 46. In some embodiments, memory 46 may store parameter sets 48 that are available to be selected by patient 12 for delivery of neurostimulation therapy. In some embodiments, processor 44 may record usage information 50, and store usage information 50 in memory 46. Memory 46 may also include program instructions that, when executed by processor 44, cause IMD 14 to perform the functions ascribed to IMD 14 herein. Memory 46 may include any volatile, non-volatile, fixed, removable, magnetic, optical, or electrical media, such as a RAM, ROM, CD-ROM, hard disk, removable magnetic disk, memory cards or sticks, NVRAM, EEPROM, flash memory, and the like.

IMD 14 also includes a telemetry circuit 52 that allows processor 44 to communicate with clinician programmer 20 and patient programmer 26. Processor 44 may receive programs to test on patient 12 from clinician programmer 20 via telemetry circuit 52 during programming by a clinician. Where IMD 14 stores parameter sets 48 in memory 46, processor 44 may receive parameter sets 48 from clinician programmer 20 via telemetry circuit 52 during programming by a clinician, and later receive parameter set selections made by patient 12 from patient programmer 26 via telemetry circuit 52. Where patient programmer 26 stores the parameter sets, processor 44 may receive parameter sets selected by patient 12 from patient programmer 26 via telemetry circuit 52.

Figure 3:
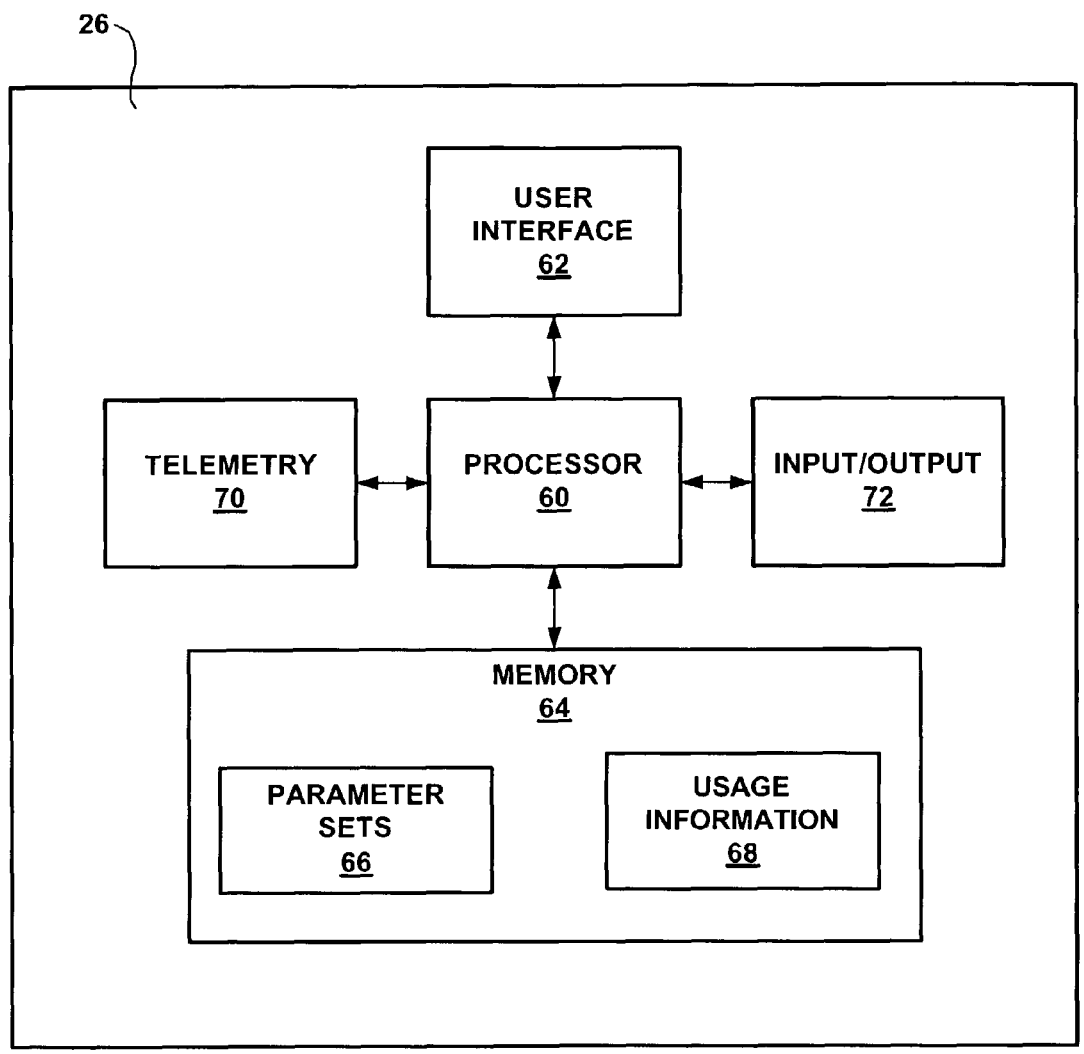
FIG. 3 is a block diagram illustrating an example patient programmer that allows a patient to control delivery of neurostimulation therapy by an implantable medical device, and collects neurostimulation therapy usage information.

FIG. 3 is a block diagram illustrating an example configuration of patient programmer 26. Patient 12 may interact with a processor 60 via a user interface 62 in order to control delivery of neurostimulation therapy as described herein. User interface 62 may include display 28 and keypad 30, and may also include a touch screen or peripheral pointing devices as described above. Processor 60 may also provide a graphical user interface (GUI) to facilitate interaction with patient 12, as will be described in greater detail below. Processor 60 may include a microprocessor, a controller, a DSP, an ASIC, an FPGA, discrete logic circuitry, or the like.

Patient programmer 26 also includes a memory 64. In some embodiments, memory 64 may store parameter sets 66 that are available to be selected by patient 12 for delivery of neurostimulation therapy. In some embodiments, processor 60 may record usage information 68, and store usage information 68 in memory 64. Memory 64 may also include program instructions that, when executed by processor 60, cause patient programmer 26 to perform the functions ascribed to patient programmer 26 herein. Memory 64 may include any volatile, non-volatile, fixed, removable, magnetic, optical, or electrical media, such as a RAM, ROM, CD-ROM, hard disk, removable magnetic disk, memory cards or sticks, NVRAM, EEPROM, flash memory, and the like.

Patient programmer 26 also includes a telemetry circuit 70 that allows processor 60 to communicate with IMD 14, and input/output circuitry 72 that to allow processor 60 to communicate with clinician programmer 20. Processor 60 may receive parameter set selections made by patient 12 via user interface 62, and may either transmit the selection or the selected parameter set to IMD 14 via telemetry circuitry 70 for delivery of neurostimulation therapy according to the selected parameter set. Where patient programmer 26 stores parameter sets 66 in memory 64, processor 60 may receive parameter sets 66 from clinician programmer 20 via input/output circuitry 72 during programming by a clinician. Circuitry 72 may include transceivers for wireless communication, appropriate ports for wired communication or communication via removable electrical media, or appropriate drives for communication via removable magnetic or optical media.

Figure 4:
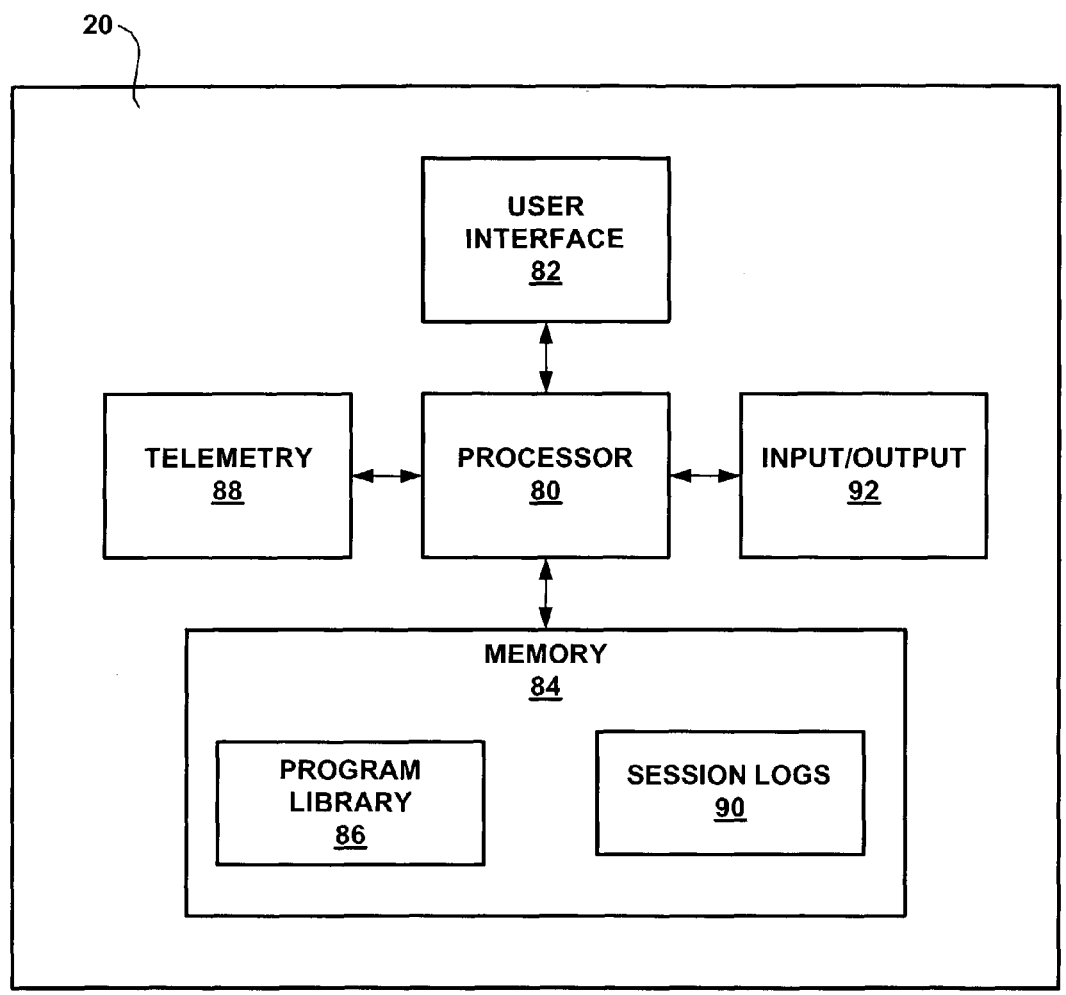
FIG. 4 is a block diagram illustrating an example clinician programmer that allows a clinician to program neurostimulation therapy for a patient by creating parameter sets.

FIG. 4 is a block diagram illustrating an example configuration of clinician programmer 20. A clinician may interact with a processor 80 via a user interface 82 in order to program neurostimulation therapy for patient 12 as described herein. User interface 82 may include display 22 and keypad 24, and may also include a touch screen or peripheral pointing devices as described above. Processor 80 may also provide a graphical user interface (GUI) to facilitate interaction with a clinician, as will be described in greater detail below. Processor 80 may include a microprocessor, a controller, a DSP, an ASIC, an FPGA, discrete logic circuitry, or the like.

Clinician programmer 20 also includes a memory 84. Memory 84 may include program instructions that, when executed by processor 80, cause clinician programmer 20 to perform the functions ascribed to clinician programmer 20 herein. Memory 84 may include any volatile, non-volatile, fixed, removable, magnetic, optical, or electrical media, such as a RAM, ROM, CD-ROM, hard disk, removable magnetic disk, memory cards or sticks, NVRAM, EEPROM, flash memory, and the like.

A clinician may program neurostimulation therapy for patient 12 by specifying programs or selecting previously specified program to test on patient 12. The clinician may interact with the GUI and user interface 82 in order to specify programs, or to select programs from a program library 86 that includes previously specified programs. Program library 86 may be stored within a non-volatile medium of memory 84. Processor 80 transmits the selected or specified programs to IMD 14 for delivery to patient 12 via a telemetry circuit 88.

Processor 80 may maintain a session log 90 for patient 12 during programming of neurostimulation therapy for patient 12 by the clinician. Upon delivery of a selected or specified program, clinician may receive feedback relating to the tested program from patient 12, and enter rating information relating to the tested program via the GUI and user interface 82. Processor 80 may store information identifying tested programs and associated rating information as part of session log 90. Information identifying tested programs may include the parameters for the tested programs. Processor 80 may present a listing of tested programs and associated rating information to the clinician in order to facilitate selection of programs to create parameter sets. Session logs 90 may be stored in a volatile medium of memory 84, or may be stored within a non-volatile medium of memory 84, e.g. within a database of patient information.

Processor 80 may transmit parameter sets created by the clinician to IMD 14 via telemetry circuitry 88, or to patient programmer 26 via input/output circuitry 92. In this manner, processor 80 may be used to control IMD 14 to deliver neurostimulation therapy for purposes of evaluating effectiveness of particular programs. I/O circuitry 92 may include transceivers for wireless communication, appropriate ports for wired communication or communication via removable electrical media, or appropriate drives for communication via removable magnetic or optical media.

FIG. 5-10 are diagrams illustrating an example graphical user interface (GUI) 100 that may be provided by clinician programmer 20 to allow a clinician to program neurostimulation therapy for patient 12 using a session log 90. The configuration of GUI 100 illustrated in FIG. 5-10 is merely exemplary and is provided for purposes of illustration.

Figure 5:
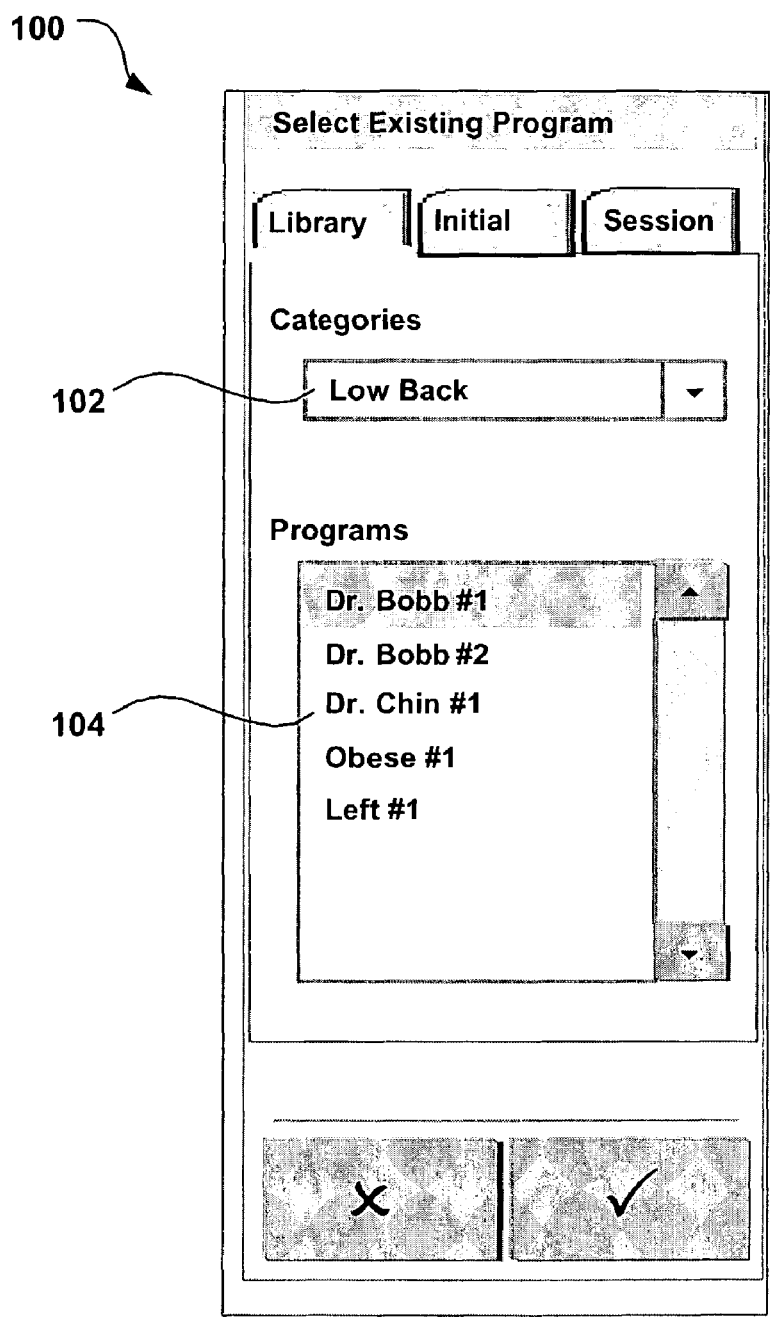
FIG. 5-10 are diagrams illustrating an example graphical user interface that may be provided by a clinician programmer to allow a clinician to program neurostimulation therapy using a session log.

FIG. 5 illustrates a portion of GUI 100 that may be used by a clinician to locate and retrieve programs stored as program library 86 within a memory. The clinician may use GUI 100 to select a program stored within program library 86 to test on patient 12. Storing programs within program library 86 may allow the clinician to quickly retrieve programs that have been previously identified as particularly effective programs. Thus, the clinician may not need to start from a blank slate in order to program neurostimulation therapy for each new patient 12.

Programs may be stored within program library 86 according to a set of hierarchical categories. Each category may be related to a characteristic of neurostimulation therapy programs. For example, programs may be stored within program library 86 according to a directory structure that is structured according to the hierarchical categories. Exemplary categories include IMD types, lead types, lead configurations, therapy indications, symptoms, body regions, patient types, clinician names, and patient names. As shown in FIG. 5, GUI 100 may include fields 102 and 104 to allow the clinician to navigate a directory structure of program library 86 and locate a program therein. Field 102 may identify a body region, whereas field 104 may identify programs according to a variety of identifiers such as physician name. The directory structure of program library 86 may allow the clinician to more easily locate relevant programs within program library 86.

Figure 6:
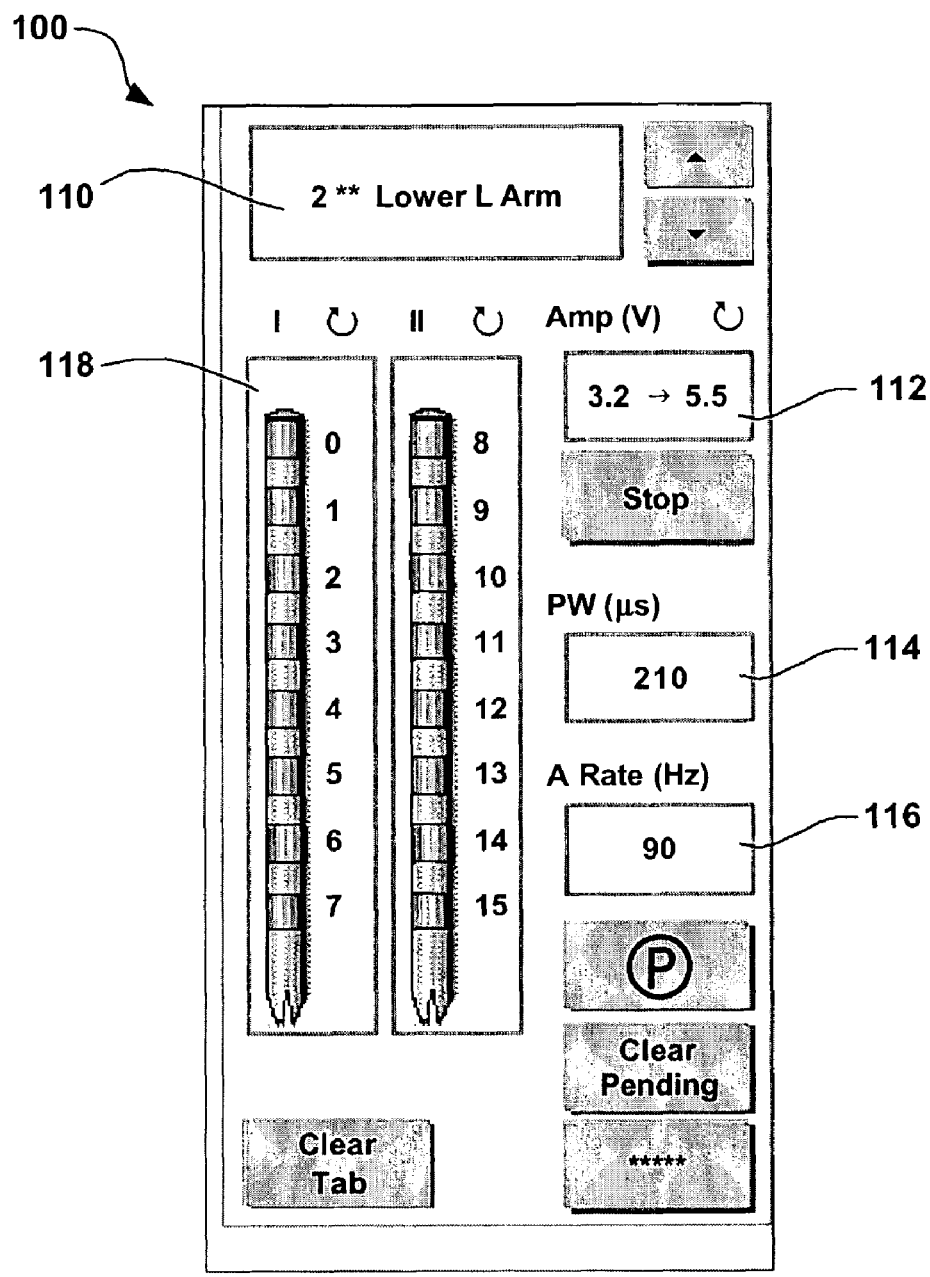

FIG. 6 illustrates a portion of GUI 100 that may be used by a clinician to specify a new program to test on patient 12. GUI 100 may, as shown in FIG. 6, include a field 110 which the clinician may use to name a new program for the session log 90. GUI 100 also includes fields 112-116, which the clinician may use to program parameter values such as pulse amplitude, pulse width and pulse rate for the new program, and a field 118, which the clinician may use to select particular electrodes 40 and assign polarities of selected electrodes 40 for the program. In some embodiments, programs imported from program library 86 may be displayed via this portion of GUI 100 for renaming or modification.

Figure 7:
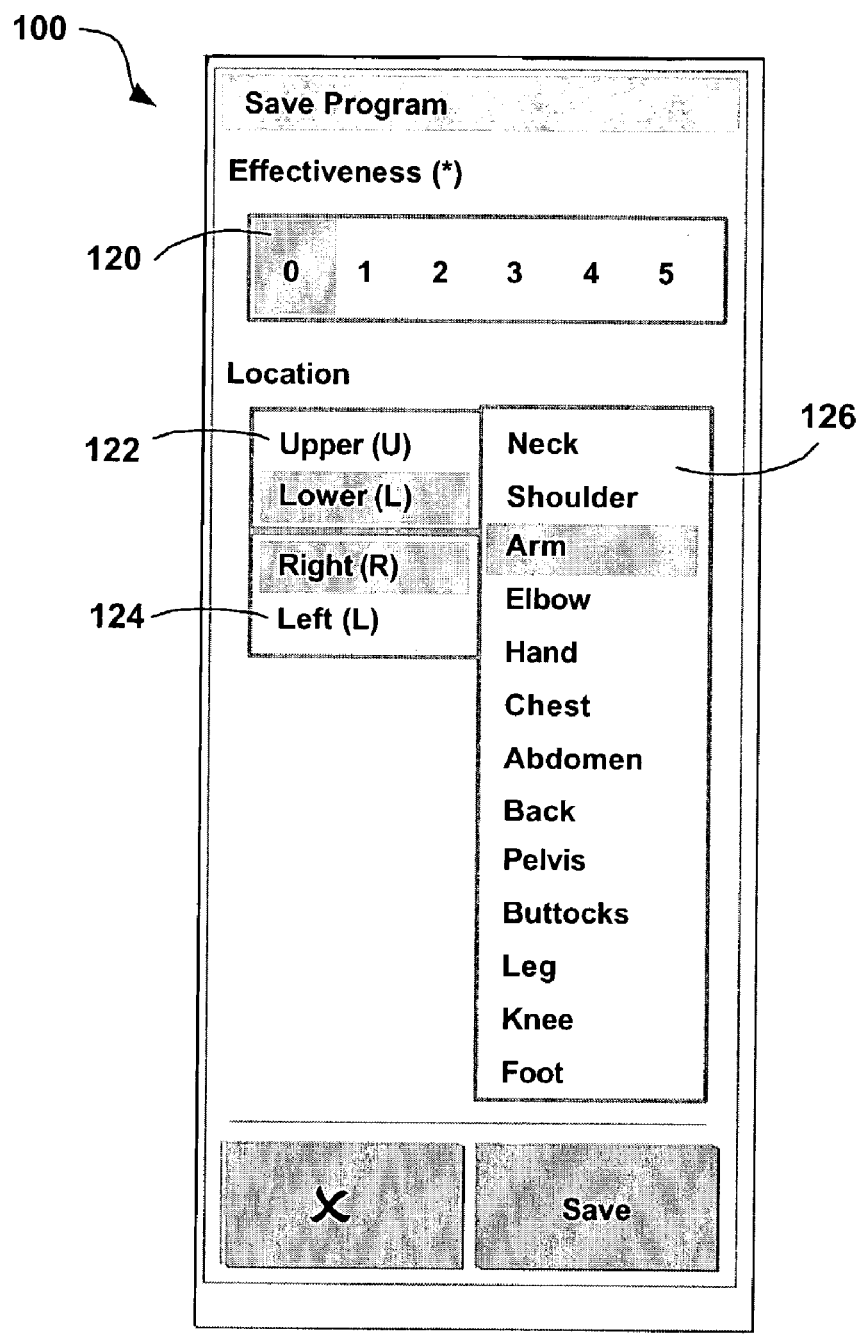

FIG. 7 illustrates a portion of GUI 100 that may be used by a clinician to enter rating information for a program tested on patient 12. Rating information may include information relating to the degree of effectiveness of the tested program in treating symptoms of patient 12 and the degree of side effects experienced by patient 12 due to the delivery of neurostimulation therapy according to the program. Effectiveness of a program may encompass both the coverage area provided by the program and degree of symptom relief. Rating information may also, for example, include information relating to the performance of IMD 14 during delivery of neurostimulation according to the program.

Rating information may include information relating to at least one metric for rating the program, and may, as illustrated in FIG. 7, include numerical values. For example, as shown in FIG. 7, the clinician is prompted to enter a numerical rating for the effectiveness of the tested program using field 120. Multiple metrics may be used. For example, the clinician may provide a rating for the severity of side effects in general, for specific side effects, or for more particular measures of the effectiveness of a particular type of therapy. For example, different metrics may be applicable to pain, movement disorders, and gastrointestinal disorders. The clinician may select the metrics to be used to evaluate tested programs.

Field 120 is merely exemplary, and numerical values for metrics may be entered using any type of field, such as a text box, drop-down menu, slider-bar, or the like. Moreover, rating information is not limited to numerical values, and may also, for example, include percentages or textual descriptions of the effectiveness, side-effects, and the like. The clinician may use fields 122-126 to identify the location of the effectiveness of the tested program as reported by patient 12, and this location information may be used as a name for the tested program within session log 90.

Figure 8:
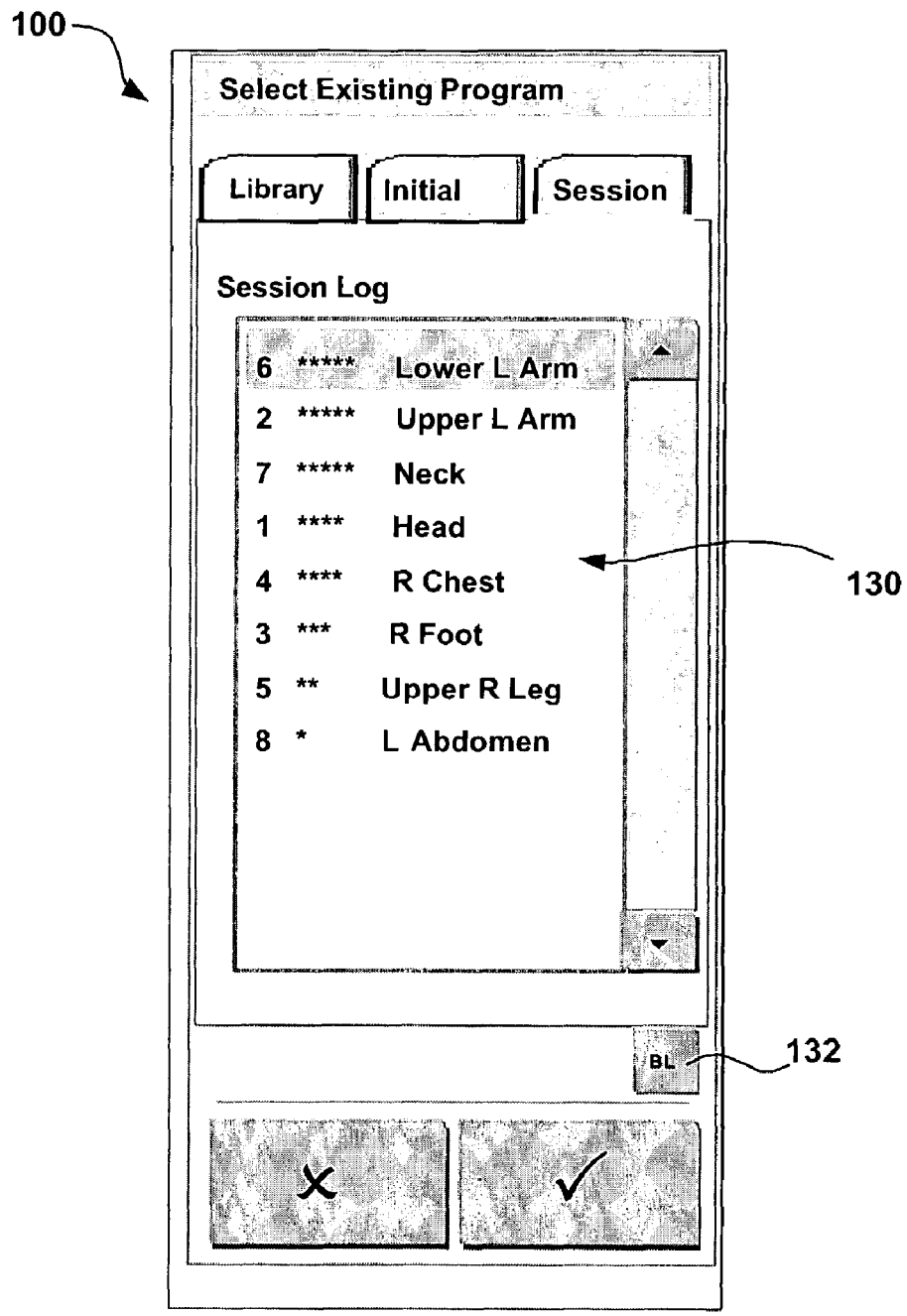

FIG. 8 illustrates a portion of GUI 100 that may be used by clinician programmer 20 to present a list 130 of the programs identified within session log 90 and associated rating information. As shown in FIG. 8, list 130 may be ordered according to the rating information. In embodiments where more than one metric is used to rate programs, list 130 may be ordered according to a metric selected by the clinician, or an overall rating may be calculated based on a number of metrics, and the list may be ordered according to the overall rating. For an overall rating, weighting factors, which may be selected by the clinician, may be applied to the metrics.

Ordering of list 130 according to rating information may facilitate comparison of the programs and quick program selection by the clinician. The clinician may select program from list 130 for inclusion in parameter sets based on the rating information. List 130 may also facilitate retransmission of multiple programs from list 130 to IMD 14 for side-by-side comparison, e.g., if multiple programs directed toward a particular symptom are closely rated. In such embodiments, clinician programmer 20 may prompt the clinician to add one of the compared programs to a parameter set, or remove one of the compared programs. In some embodiments, clinician programmer 20 may automatically select programs from session log 90 for inclusion in a parameter set based on the rating information.

Where a program is particularly ineffective, the clinician may "blacklist" the program using field 132 ("BL") to indicate that the program is undesired. Clinician programmer 20 may store an indication that the program is blacklisted, i.e., undesired based on ineffectiveness or side effects within session log 90. Blacklisting of programs within session log 90 may allow the clinician to more easily avoid retrying particularly ineffective programs with patient 12, e.g., during reprogramming at a follow-up visit. Blacklisted programs within session log 90 may be removed from list 130, or identified within list 130 using highlighting, text effects, a symbol, or the like.

Figure 9:
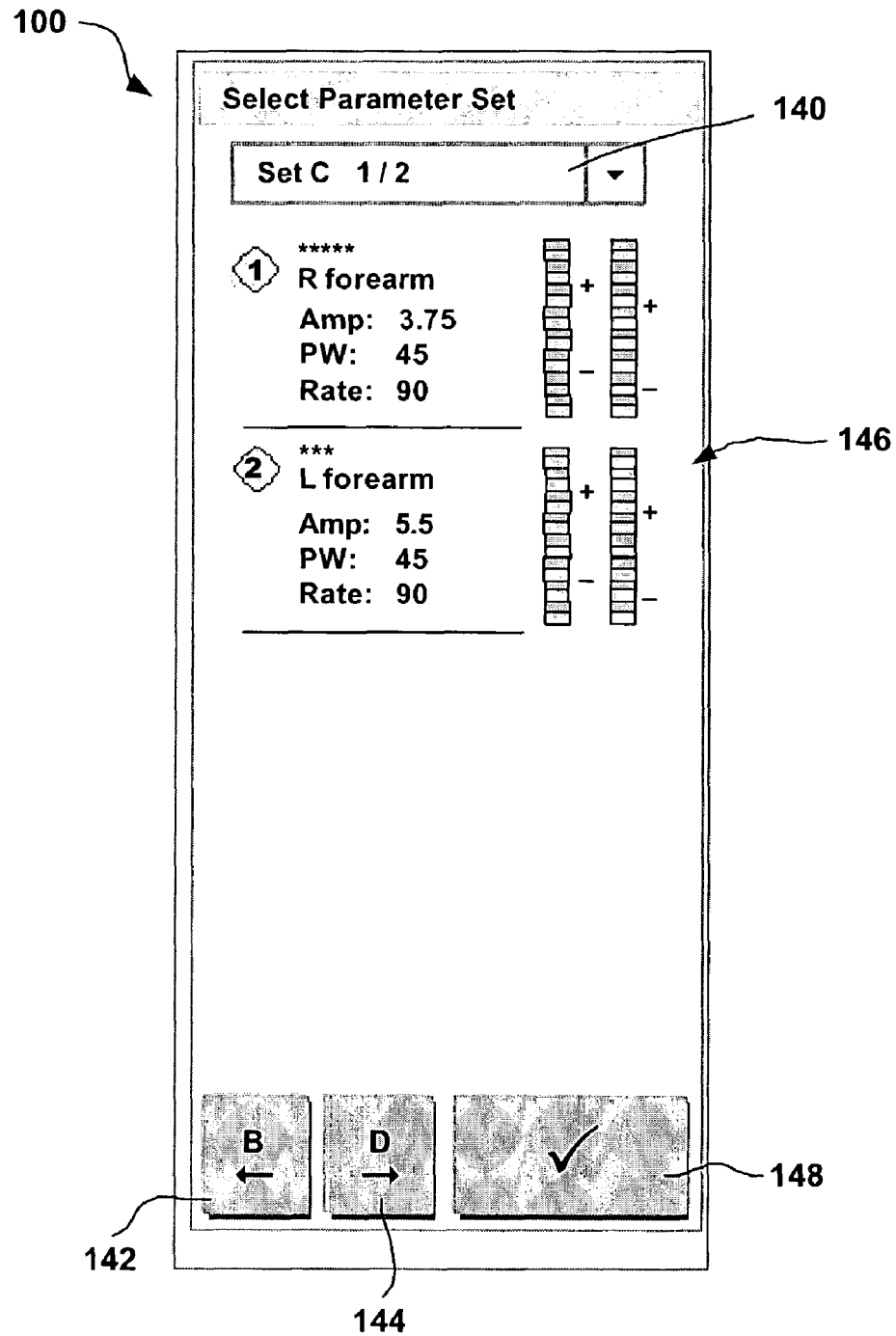

FIG. 9 illustrates a portion of GUI 100 that may be used by the clinician to review and approve the parameter sets created. As shown in FIG. 9, GUI 100 may provide fields 140-144 for selection of a parameter set. GUI 100 may display a summary 146 of the parameters of each program within a selected parameter set. Clinician may approve the parameter sets using field 148, and clinician programmer 20 may then transmit the parameter sets to one or both of IMD 14 via telemetry circuit 88 and patient programmer 26 via input/output circuit 92.

Figure 10:
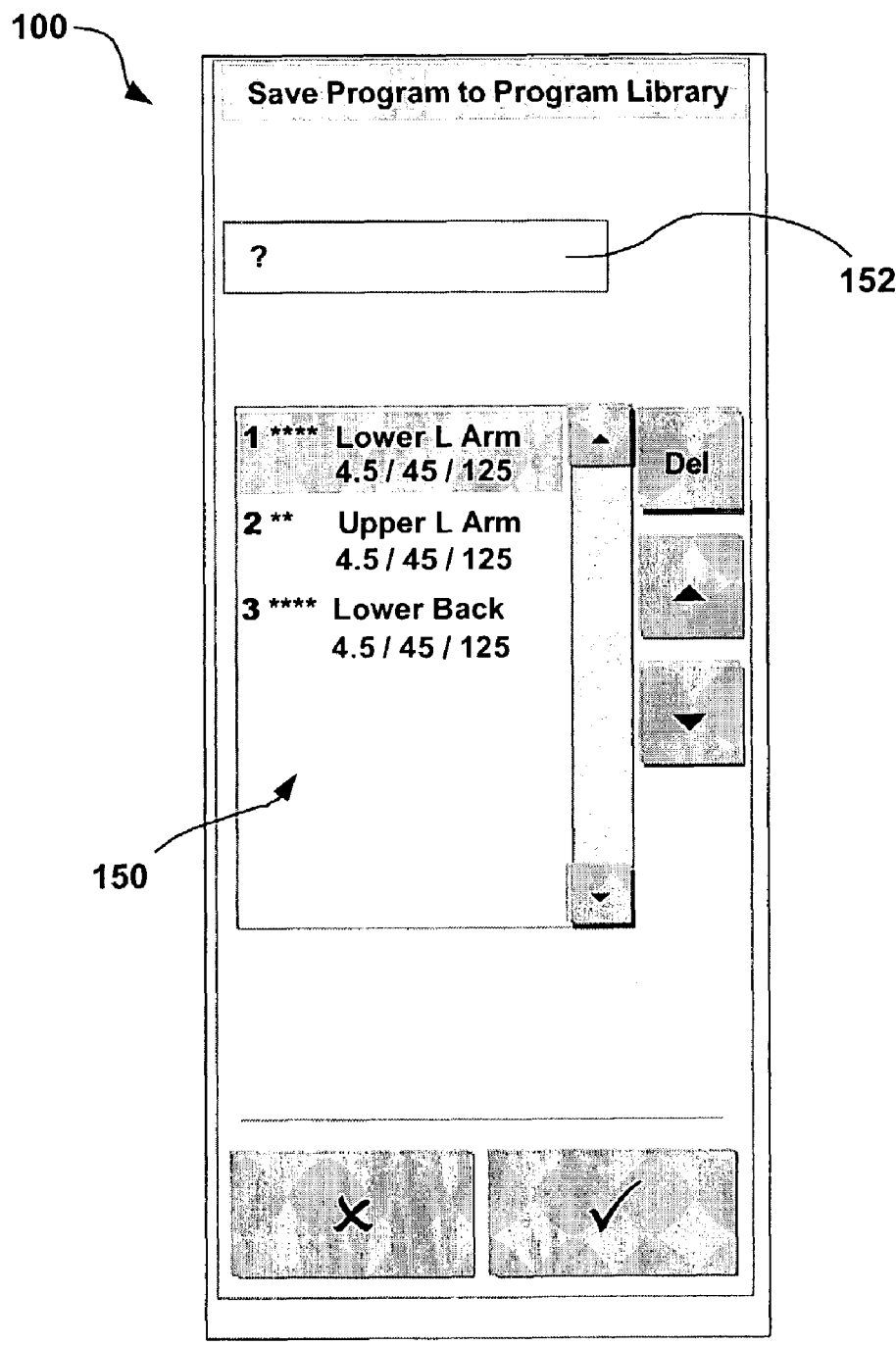

FIG. 10 illustrates a portion of GUI 100 that may be used by the clinician to store programs that appear particularly effective, e.g., from the programming session or after a follow-up visit, within program library 86. As shown in FIG. 10, GUI 100 may display a list 150 of programs from session log 90 and associated rating information. The clinician may select a program from list 150, and name it for storage in program library using field 152. Although not shown in FIG. 10, the clinician may categorize the program via GUI 100 so that the program is stored appropriately according to the directory structure of program library 86.

List 150 may also be created based on programs stored within IMD 14 or patient programmer 26 at a follow-up visit. Patient 12 may have adjusted these programs. Thus, the clinician may also store effective programs discovered by patient 12 in program library 86. Moreover, programs may be identified during a follow-up visit based on the frequency of their use by patient 12 reflected in usage information 50,68 stored by one or both of IMD 14 and patient programmer 26. Usage information 50,68 pertaining to a program selected for inclusion in program library 86, or a summary thereof, may be stored in program library 86 with the program.

Figure 11:
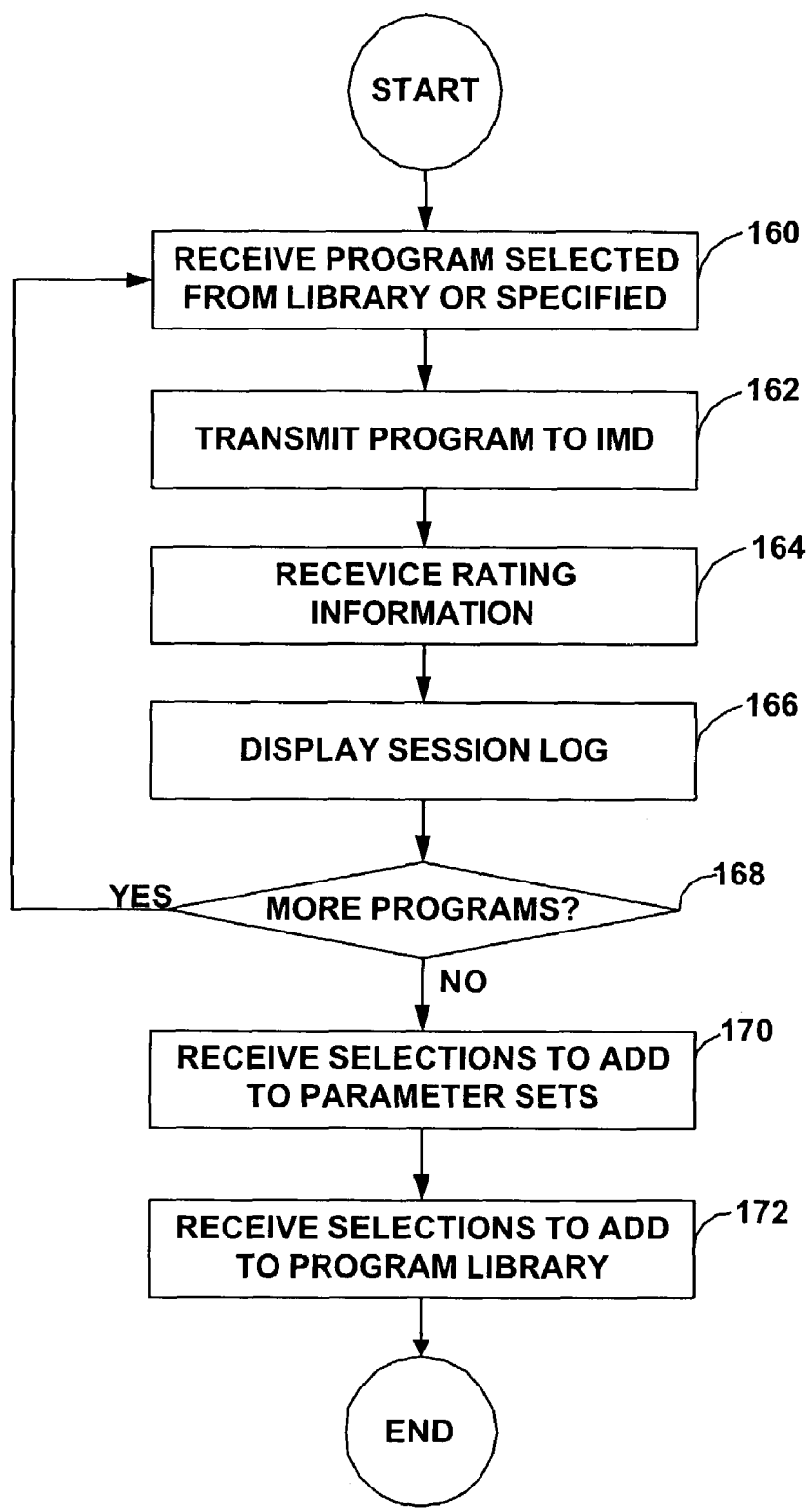
FIG. 11 is a flowchart illustrating a method that may be employed by a clinician programmer to allow a clinician to program neurostimulation therapy using a session log.

FIG. 11 is a flowchart illustrating a method that may be employed by clinician programmer 20 to allow a clinician to program neurostimulation therapy using session log 90. Clinician programmer 20 receives a program to test that is selected from program library 86, or specified by the clinician (160), and transmits the program to IMD 14 to control delivery of neurostimulation therapy according to the program (162). The clinician receives feedback from patient 12, and records rating information as described above (164).

Clinician programmer 20 displays a list 130 of programs and rating information from session log 90 (166), which may be ordered according to the rating information, and may update the list after each new program is tested (168). When the clinician has completed testing programs, clinician programmer 20 may receive selections from list 130 for creation of parameter sets (170). Clinician programmer 20 may also receive selections made by the clinician for addition to program library 86 (172).

Figure 12:
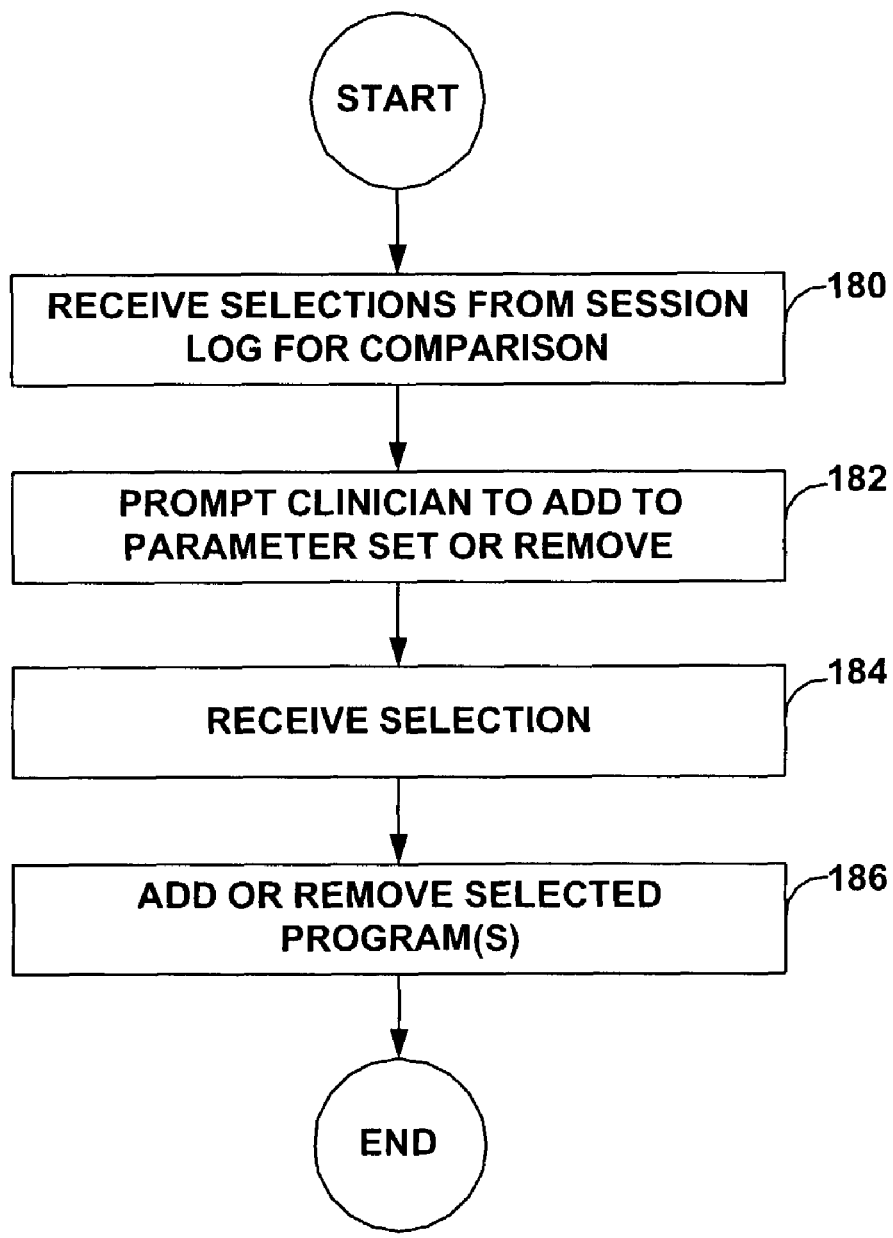
FIG. 12 is a flowchart illustrating another method that may employed by a clinician programmer to allow a clinician to program neurostimulation therapy using a session log.

FIG. 12 is a flowchart illustrating another method that may be employed by clinician programmer 20 to allow a clinician to program neurostimulation therapy using session log 90. In particular, FIG. 12 illustrates a method that may be employed by clinician programmer 20 to facilitate retransmission and side-by-side comparison of programs stored within session log 90. Clinician programmer 20 receives selections made by the clinician from list 130, and retransmits the selected programs to IMD 14 to control delivery of neurostimulation therapy according to the retransmitted programs (180). After delivery according to the retransmitted programs, clinician programmer 20 may prompt the clinician to select one or more of the compared programs for addition to a parameter set or removal from list 130, receive a selection made by the clinician, and add or remove the selected programs (182-186).

Figure 13:
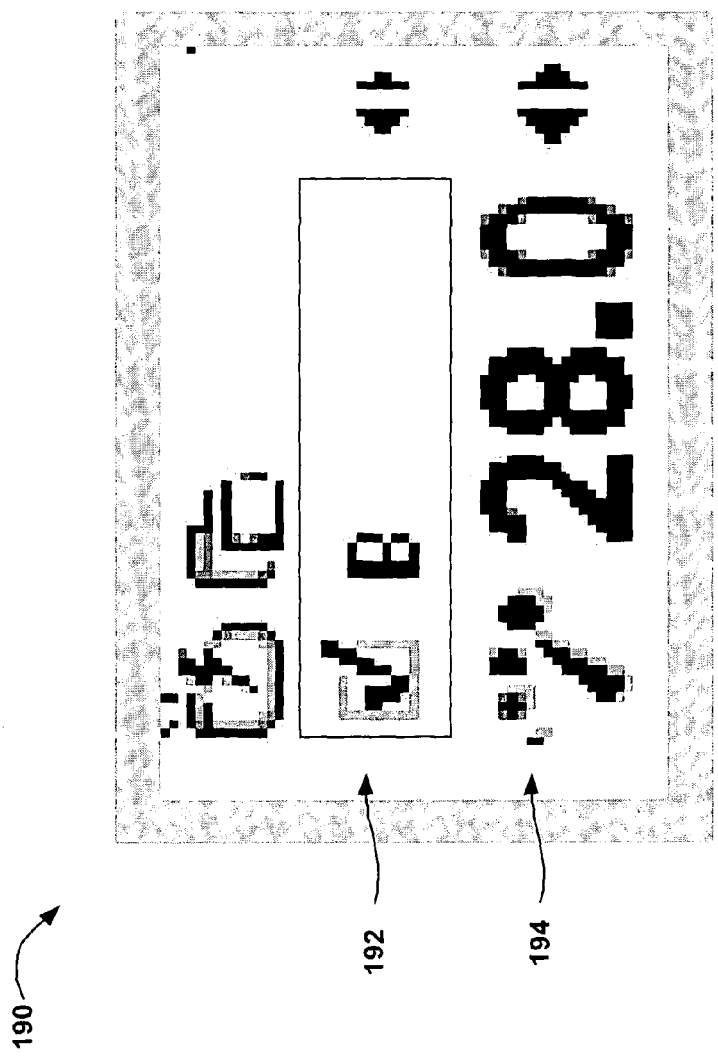
FIG. 13 is a diagram illustrating an example graphical user interface that may be provided by a patient programmer to allow a patient to control delivery of neurostimulation therapy by an implantable medical device.

FIG. 13 is a diagram illustrating an example GUI 190 that may be provided by patient programmer 26 to allow patient 12 to control delivery of neurostimulation therapy by IMD 14. In general, parameter sets stored within one or both of IMD 14 and patient programmer 26 and available for selection or adjustment by patient 12 may be organized into one or more lists. Patient 12 may scroll through a list of available parameters sets using field 192 of GUI 190. A name for each parameter set and an indication as to which parameter set is currently activated may be displayed via field 192.

A field 194 may allow patient 12 to scroll through the various parameters of the programs of a selected parameter set. Patient 12 may select a parameter, and adjust the value of that parameter within limits established by a clinician. Patient 12 may also make adjustments to the value of a particular parameter throughout all of the programs of a parameter set, e.g., if patient 12 is experiencing increased pain at all locations, patient 12 may increase the pulse amplitude of all programs within the currently active set. Where adjustments are made to a particular parameter throughout all of the programs of a parameter set, the adjustment may be scaled for each program in order to maintain a ratiometric balance between the programs.

Shortcuts may be provided to frequently used parameter sets. For example GUI 190 may provide icons for direct activation of frequently used parameter sets. Keys of keypad 30 may also be associated with frequently used parameter sets, and used by patient 12 for direct activation of those parameter sets.

Figure 14:
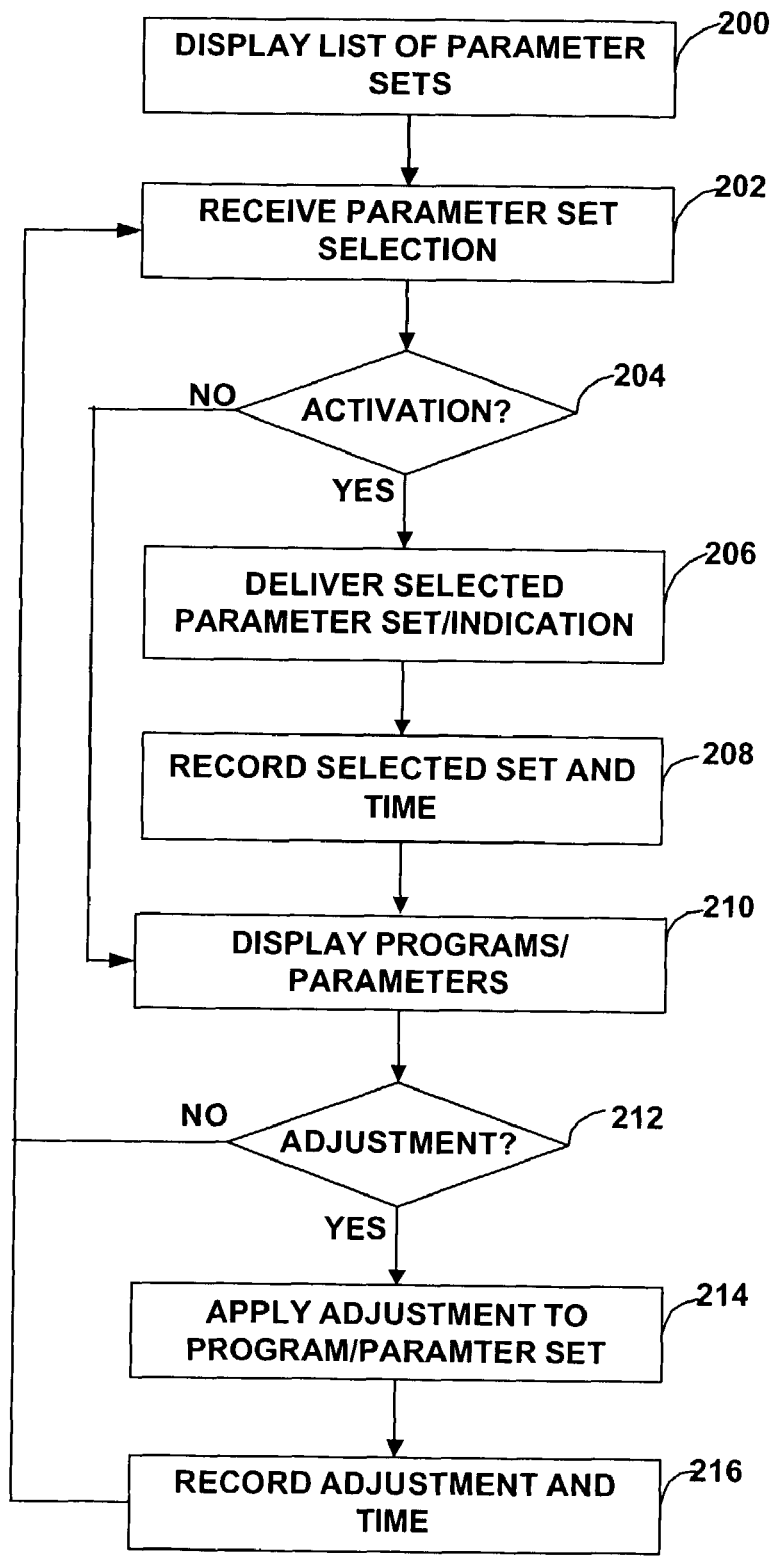
FIG. 14 is a flowchart illustrating a method that may be employed by one or both of a patient programmer and an implantable medical device to allow a patient to control neurostimulation therapy and record neurostimulation therapy usage information.

FIG. 14 is a flowchart illustrating a method that may be employed by one or both of patient programmer 26 and IMD 14 to allow patient 12 to control delivery of neurostimulation therapy, and record neurostimulation therapy usage information 50, 68. Patient programmer 26 displays a list of parameter sets 48, 66 (200), and receives a parameter set selection made by patient 12 (202). In embodiments where parameter sets 48 are stored by IMD 14, patient programmer 26 may receive list of parameter sets from IMD 14.

If patient programmer 26 receives a command from patient to activate the selected parameter set (204), patient programmer 26 will direct IMD 14 to deliver neurostimulation therapy according to the selected parameter set (206). In embodiments where parameter sets 66 are stored by patient programmer 26, patient programmer 26 transmits the selected parameter set to IMD 14. In embodiments where parameter sets 48 are stored by IMD 14, patient programmer 26 may transmit an indication of the selected parameter set to IMD 14.

One or both of patient programmer 26 and IMD 14 may also record parameter set usage information 50, 68 by recording which set was selected and the time of set activation (208). Patient programmer 26 and/or IMD) 14 may alternatively record usage information 50, 68 by periodically determining whether therapy is activated and which parameter set is active.

Patient programmer 26 displays programs and program parameters for the selected parameter set (210). Patient programmer 26 may receive an adjustment to the selected parameter set (212) from the patient, and apply the adjustment to a selected parameter for a single program or for the entire parameter set (214). Where parameter sets 48 are stored in IMD 14, or where the parameter set is active, patient programmer 26 may direct IMD 14 to apply the adjustment. One or both of patient programmer 26 and IMD 14 may record usage information 50,68 by recording the adjustment made and the time of adjustment (216).

Figure 15:
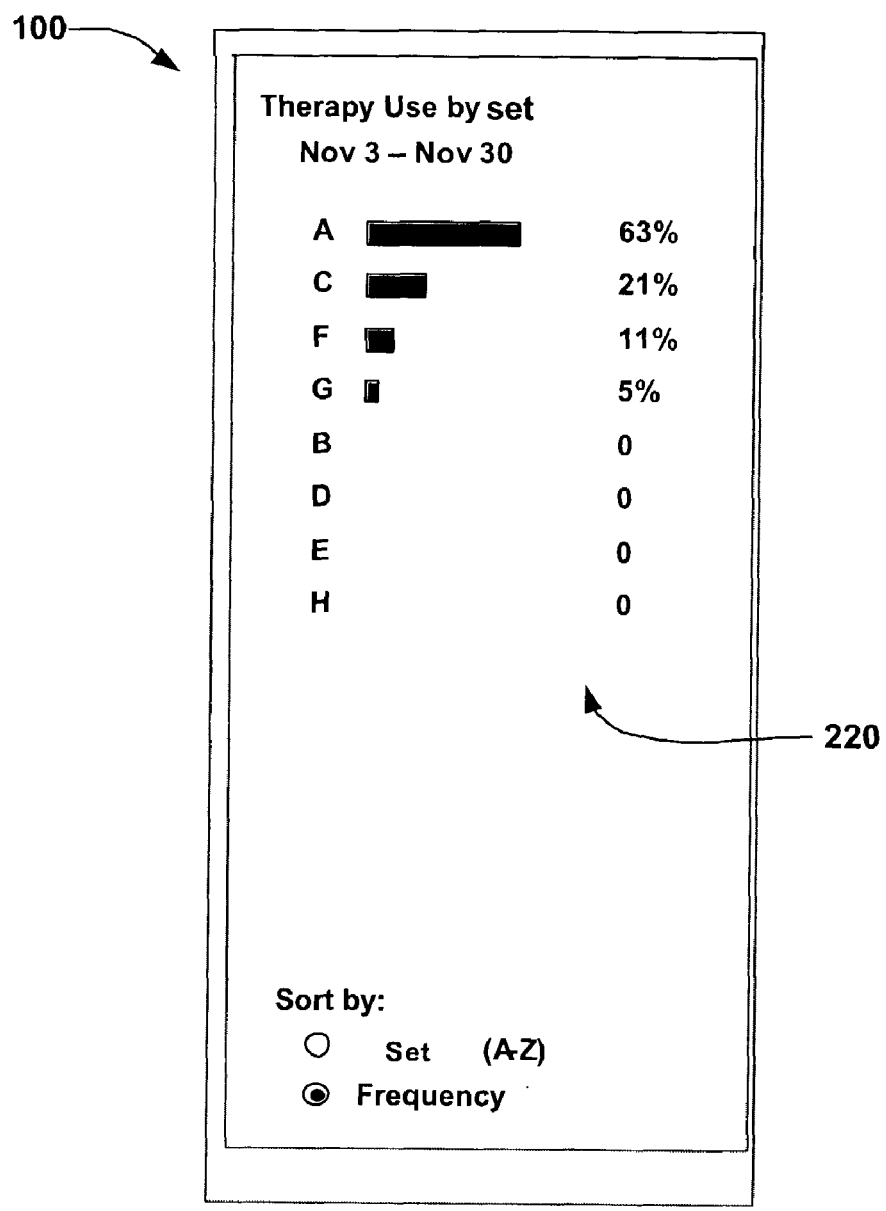
FIG. 15-17 are diagrams illustrating a graphical user interface that may be provided by a clinician programmer in order to provide usage information to a clinician.
Figure 16:
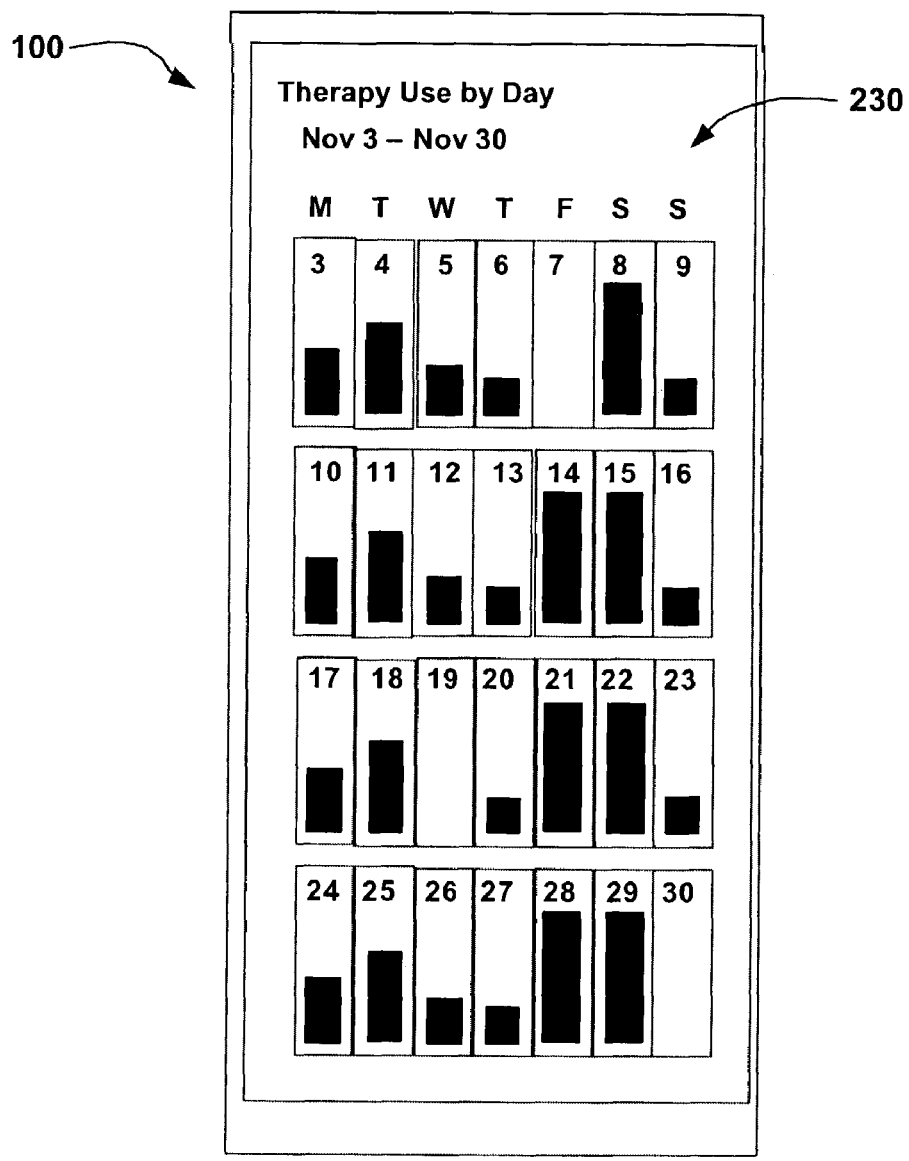
Figure 17:
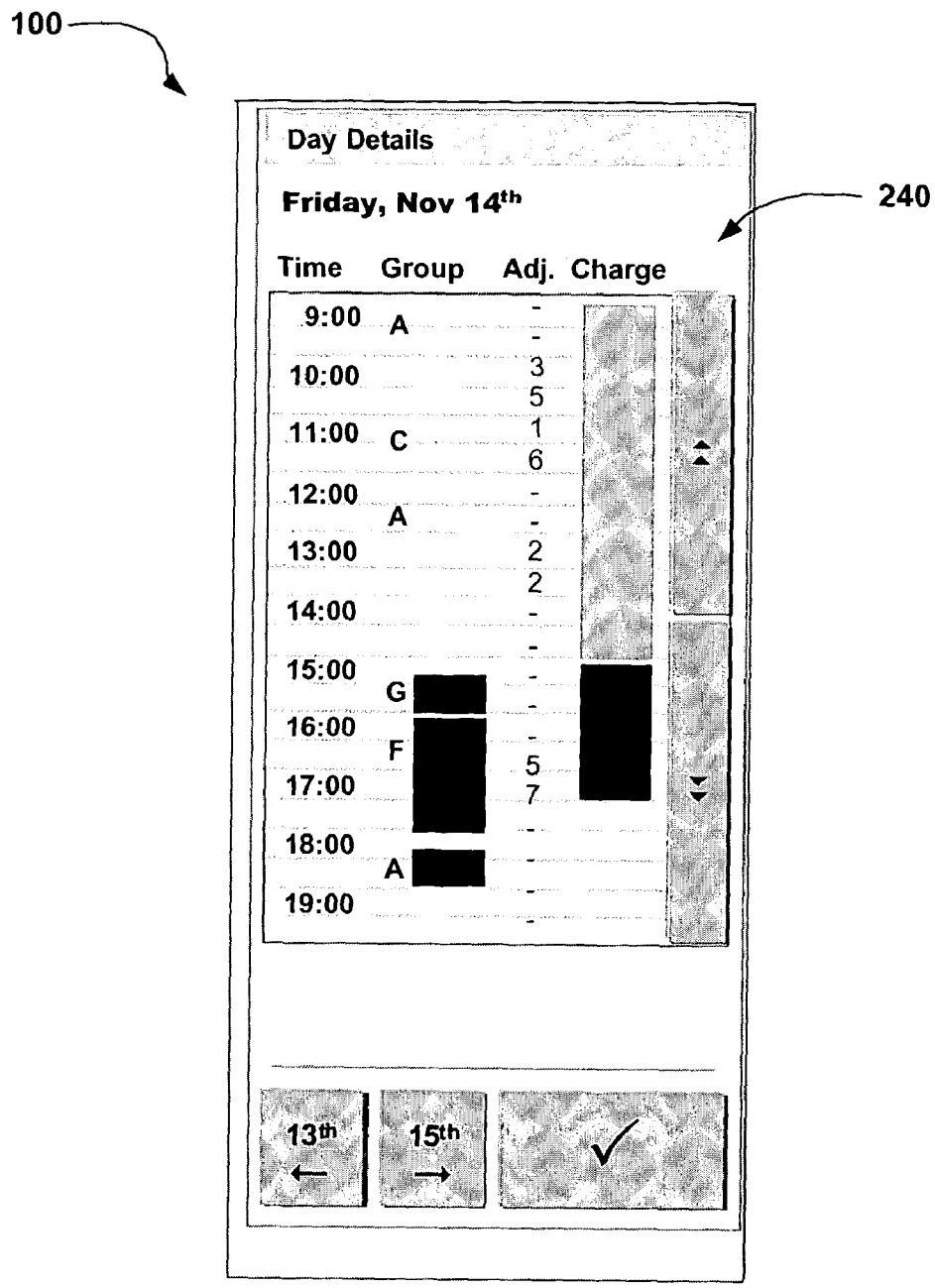

FIG. 15-17 are diagrams illustrating techniques that may be employed by clinician programmer 26 to present neurostimulation therapy usage information 50,68 to a clinician via GUI 100. The invention is not limited to the illustrated forms of presenting usage information to the clinician, however. A variety of diagrams, histograms, charts, graphs, summaries, or the like may be used to present usage information 50,68 to the clinician. As one example in addition to the forms of presenting usage information discussed below, clinician programmer may present a trend graph or the like illustrating the value of a program parameter, such as amplitude, over time.

As shown in FIG. 15, clinician programmer 26 may present a histogram 220 that illustrates percentages of the total neurostimulation therapy use for each parameter set. Histogram 220 may be used by the clinician to determine which parameter sets were preferred or effective, and which parameter sets were not preferred or ineffective. The clinician may eliminate unused parameter sets, and add additional parameter sets that are similar to the preferred or effective parameter sets. Clinician programmer 20 may mark unused parameter sets for removal from a list. A similar histogram may be used to illustrate percentages of the total neurostimulation therapy use for individual programs.

FIG. 16 illustrates a calendar-view diagram 230 that may be presented by clinician programmer 26. Diagram 230 illustrates overall therapy usage each day, and may be used by the clinician to evaluate day-to-day changes in the symptoms of patient 12. Similar diagrams may be used to illustrate month-to-month, or week-to-week changes in therapy usage. Trends in the data illustrated by diagram 230 may suggest a need to provide new parameter sets or programs to address changes in symptoms of patient 12.

FIG. 17 illustrates a day-view diagram 240 that may be presented by clinician programmer 26. For a selected day, diagram 240 illustrates which, if any, parameter set was activated at any given time. Diagram 240 also illustrates the time of adjustments to parameter sets made during the day. Diagram 240 may be used by the clinician to evaluate cyclical changes in the activity or symptoms of patient 12 throughout a day. Trends in the data illustrated by diagram 240 may suggest a particular activity or time of day for which new parameter sets or programs would be beneficial.

Figure 18:
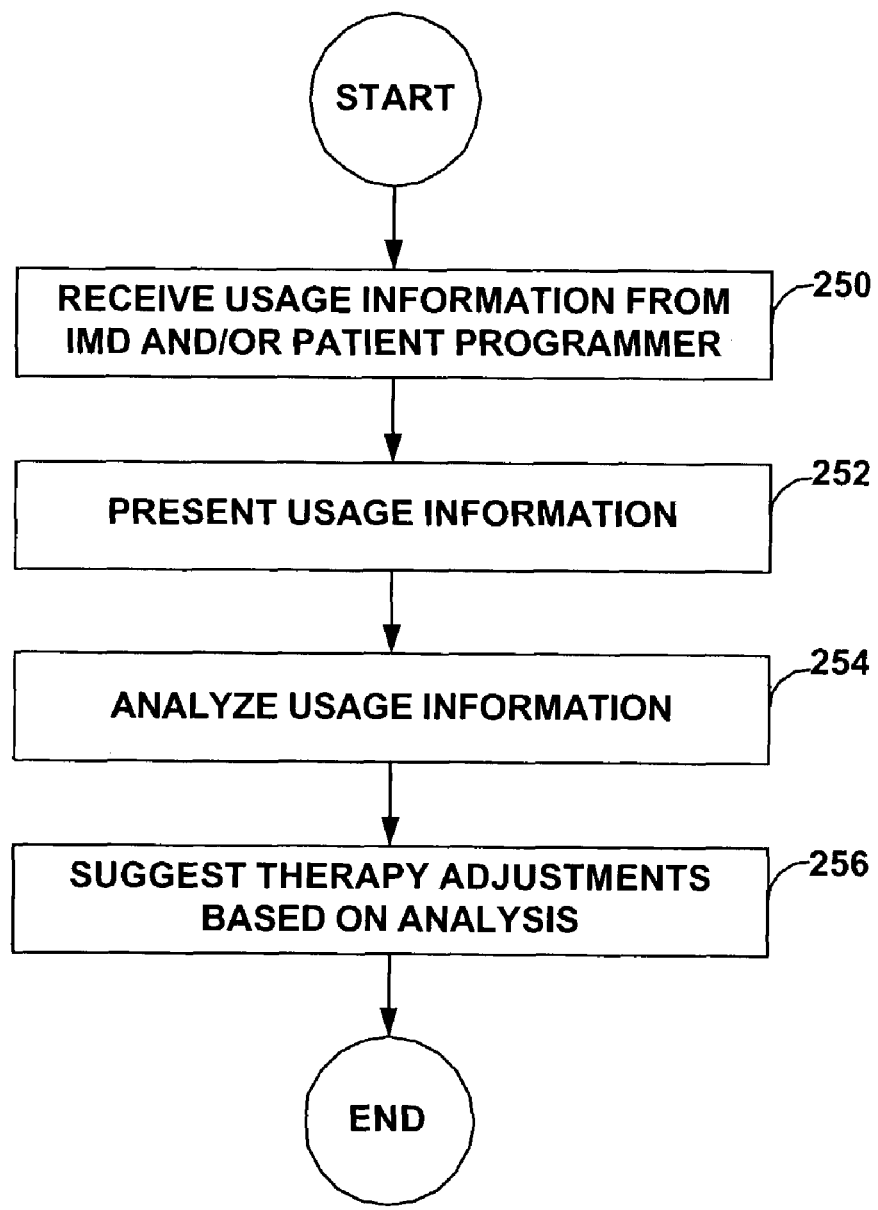
FIG. 18 is a method that may be employed by a clinician programmer to suggest neurostimulation therapy adjustments based on usage information.

FIG. 18 is a method that may be employed by clinician programmer 20 to suggest neurostimulation therapy adjustments based on usage information 50,68. Clinician programmer 20 receives usage information 50,68 from one or both of IMD 14 and patient programmer 26 (250), and presents usage information 50,68 to the clinician as described above (252). Clinician programmer 20 analyzes usage information 50,68 (254), and suggests therapy adjustments based on the analysis (256). For example, clinician programmer 20 may identify a frequently used parameter set, and suggest that additional programs that are similar to the programs of the frequently used parameter set be added to the therapy for patient 12. Clinician programmer 20 may identify additional programs by comparing the programs of the frequently used parameter set to programs located within at least one of session log 86 and program library 90. Clinician programmer 20 may also identify infrequently used parameter sets and mark them for removal from a list. By analyzing the usage information and suggesting therapy modifications to the clinician, the clinician programmer may reduce the amount of time necessary for the clinician to have an effective follow-up visit with patient 12.

Various embodiments of the invention have been described. However, one skilled in the art will appreciate that various modifications may be made to these embodiments without departing from the scope of the invention. For example, although the non-volatile medium that stores program library 90 has been described as integral with clinician programmer 20, or a removable medium for clinician programmer 20, the non-volatile medium may be located on a computer separate from clinician programmer 20. Clinician programmer 20 may communicate with the computer via any of the wireless or wired methods discussed above, or input/output circuitry 92 may include a network interface to access program library 90 via a computer network.

Further, program libraries 90 may facilitate program sharing. A program library 90 or portion thereof containing recommended programs may be distributed by, for example, an implantable medical device or lead manufacturer, or various luminaries in the relevant medical disciplines. Such distributions may occur via a computer network such as the World Wide Web, or by distribution of removable media containing the programs. Clinicians within a single hospital or practice group may share a program library 90 stored on a computer available on a local area network. Clinicians may also share programs via wired or wireless connections between clinician programmers 20. For example, clinicians at a medical conference may, in this manner, share programs that they have found to be particularly effective.

As another example, IMD 14 and/or patient programmer 20 may record information in addition to the usage information. Information relating to patterns of navigation of GUI 190 by patient 12 using user interface 82 of patient programmer 26 and patient programmer 26 feature use may also be recorded, as well as information relating to the performance of IMD 14 and patient programmer 26, such as information relating to battery life, battery performance, power-on resets, resets and telemetry success. Performance information provided to the clinician may allow the clinician to identify and resolve technical problems of one or both of IMD 14 and patient programmer 26, increasing patient satisfaction with system 10. Navigation pattern and feature use information may be provided to a manufacturer of one or both of the implantable medical device and the patient programmer and used in future product development efforts, allowing the manufacturer to provide more user friendly patient programmers 26 to patients 12 in the future. These and other embodiments are within the scope of the following claims.

The invention claimed is:

1. A method comprising:
controlling an implantable medical device to deliver neurostimulation therapy to a patient according to a plurality of neurostimulation therapy programs;
for each of the neurostimulation therapy programs, receiving rating information in response to the delivery of the neurostimulation therapy according to the program, wherein the rating information comprises at least one numerical rating for effectiveness of delivery of neurostimulation therapy according to the neurostimulation therapy program in treating symptoms of the patient and at least one numerical rating for at least one side effect experienced by the patient due to the delivery of neurostimulation therapy according to the neurostimulation therapy program, wherein the numerical rating for effectiveness and the numerical rating for at least one side effect are selected by a user in response to the delivery of the neurostimulation therapy according to the neurostimulation therapy program;

associating the neurostimulation therapy programs and their respective rating information in a memory;

creating a plurality of parameter sets, each of the parameter sets including one or more of the neurostimulation programs; and including at least one of the neurostimulation therapy programs within at least one of the parameter sets based on the rating information.

2. The method of claim 1, wherein the user is a clinician.

3. The method of claim 1, wherein the at least one numerical rating for effectiveness of delivery of neurostimulation therapy includes at least one numerical rating for at least one of coverage area or degree of symptom relief provided by delivery of neurostimulation according to the neurostimulation therapy program.

4. The method of claim 1, wherein receiving the rating information comprises:

displaying a user input field for at least one of the effectiveness of delivery of neurostimulation therapy or the at least one side effect experienced by the patient due to the delivery of neurostimulation therapy to the user via a display; and receiving a numerical value selected by a user using the user input field.

5. The method of claim 1, wherein the rating information further comprises information relating to at least one of performance or life of a battery of the implantable medical device while delivering neurostimulation therapy according to the neurostimulation therapy program.

6. The method of claim 1, wherein associating the neurostimulation therapy program and the rating information comprises storing information identifying the neurostimulation therapy program and the associated rating information as part of a session log that includes information identifying neurostimulation therapy programs tested on the patient during a programming session and rating information associated with the neurostimulation therapy programs tested on the patient.

7. The method of claim 6, further comprising:

controlling the implantable medical device to deliver neurostimulation therapy according to each of a plurality of neurostimulation programs; and storing information identifying one of the neurostimulation therapy programs as part of the session log.

8. The method of claim 6, wherein storing information identifying the neurostimulation therapy program comprises storing information identifying neurostimulation therapy parameters for the neurostimulation therapy program.

9. The method of claim 8, wherein the parameters include at least one of a pulse amplitude, a pulse width, a pulse rate, selected electrodes or polarities of selected electrodes.

10. The method of claim 1, wherein including at least one of the neurostimulation therapy programs within at least one of the parameter sets comprises:

displaying the neurostimulation therapy programs and their respective rating information in a list of tested neurostimulation therapy programs;

receiving one or more selections from the list for inclusion in the parameter set.

11. The method of claim 1, wherein including at least one of the neurostimulation therapy programs within at least one of the parameter sets comprises:

prompting a user to select one of the neurostimulation therapy programs from a list of tested neurostimulation therapy programs for inclusion in the parameter set.

12. The method of claim 1, wherein the at least one numerical value for at least one side effect comprises at least one numerical value for a degree of the side effect experienced by the patient due to the delivery of the neurostimulation therapy according to the program.

13. A device comprising:

a memory to store information; and a processor programmed to:

control an implantable medical device to deliver neurostimulation therapy to a patient according to a plurality of neurostimulation therapy programs, for each of the neurostimulation therapy programs, receive rating information in response to the delivery of the neurostimulation therapy according to the program, wherein the rating information comprises at least one numerical rating for effectiveness of delivery of neurostimulation therapy according to the neurostimulation therapy program in treating symptoms of the patient and at least one numerical rating for at least one side effect experienced by the patient due to the delivery of neurostimulation therapy according to the neurostimulation therapy program, wherein the numerical rating for the effectiveness and the numerical rating for at least one side effect are selected by a user in response to the delivery of the neurostimulation therapy according to the neurostimulation therapy program, associate the neurostimulation therapy programs and their respective rating information in the memory, create a plurality of parameter sets, each of the parameter sets including one or more of the neurostimulation programs, and include at least one of the neurostimulation therapy programs within at least one of the parameter sets based on the rating information.

14. The device of claim 13, wherein the at least one numerical rating for effectiveness of delivery of neurostimulation therapy includes at least one numerical rating for at least one of coverage area or degree of symptom relief provided by delivery of neurostimulation according to the neurostimulation therapy program.

15. The device of claim 13, further comprising a display, wherein the processor receives rating information by displaying a user input field for at least one of the effectiveness of delivery of neurostimulation therapy or the at least one side effect experienced by the patient due to the delivery of neurostimulation therapy via the display, and receiving a numerical value selected by a user using the user input field.

16. The device of claim 13, wherein the rating information further comprises information relating to at least one of performance or life of a battery of the implantable medical device while delivering neurostimulation therapy according to the neurostimulation therapy program.

17. The device of claim 13, wherein the processor stores information identifying the neurostimulation therapy program and the associated rating information as part of a session log that includes information identifying neurostimulation therapy programs tested on the patient during a programming session and rating information associated with the neurostimulation therapy programs tested on the patient.

18. The device of claim 17, wherein the processor controls the implantable medical device to deliver neurostimulation therapy according to a plurality of neurostimulation programs, and stores information identifying one of the neurostimulation therapy programs as part of the session log.

19. The device of claim 17, wherein the processor stores information identifying neurostimulation therapy parameters for the neurostimulation therapy program.

20. The device of claim 19, wherein the parameters include at least one of a pulse amplitude, a pulse width, a pulse rate, selected electrodes or polarities of selected electrodes.

21. The device of claim 13, further comprising a display, wherein the processor stores an indication that the neurostimulation therapy program is an undesired program, and provides a visual indication that the neurostimulation therapy program is undesired via the display.

22. A non-transitory computer-readable medium, comprising instructions that cause a processor to:
control an implantable medical device to deliver neurostimulation therapy to a patient according to a plurality of neurostimulation therapy programs;
for each of the neurostimulation therapy programs, receive rating information in response to the delivery of neurostimulation therapy according to the program, wherein the rating information comprises at least one numerical rating for effectiveness of delivery of neurostimulation therapy according to the neurostimulation therapy program in treating symptoms of the patient and at least one metric numerical rating for at least one side effect experienced by the patient due to the delivery of neurostimulation therapy according to the neurostimulation therapy program, wherein the numerical rating for effectiveness and the numerical rating for at least one side effect are selected by a user in response to delivery of the therapy according to the neurostimulation therapy program;
associate the neurostimulation therapy programs and their respective rating information in a memory;
create a plurality of parameter sets, each of the parameter sets including one or more of the neurostimulation programs; and
include at least one of the neurostimulation therapy programs within at least one of the parameter sets based on the rating information.

23. The computer-readable medium of claim 22, wherein the at least one numerical rating for effectiveness of delivery of neurostimulation therapy includes at least one numerical rating for at least one of coverage area or degree of symptom relief provided by delivery of neurostimulation according to the neurostimulation therapy program.

24. The computer-readable medium of claim 22, wherein the instructions cause a processor to:
display a user input field for at least one of the effectiveness of delivery of neurostimulation therapy or the at least one side effect experienced by the patient due to the delivery of neurostimulation therapy via a display; and
receive a numerical value selected by a user using the user input field.

25. The computer-readable medium of claim 22, wherein the rating information further comprises information relating to at least one of performance or life of a battery of the implantable medical device while delivering neurostimulation therapy according to the neurostimulation therapy program.

26. The computer-readable medium of claim 22, wherein the instructions cause a processor to store information identifying the neurostimulation therapy program and the associated rating information as part of a session log that includes information identifying neurostimulation therapy programs tested on the patient during a programming session and rating information associated with the neurostimulation therapy programs tested on the patient.

27. The computer-readable medium of claim 26, wherein the instructions cause a processor to:
control the implantable medical device to deliver neurostimulation therapy according to each of a plurality of neurostimulation programs; and
store information identifying one of the neurostimulation therapy programs as part of the session log from the user.

28. The computer-readable medium of claim 26, wherein the instructions that cause a processor to store information identifying the neurostimulation therapy program comprise instructions that cause a processor to store information identifying neurostimulation therapy parameters for the neurostimulation therapy program.

29. The computer-readable medium of claim 28, wherein the parameters include at least one of a pulse amplitude, a pulse width, a pulse rate, selected electrodes, or polarities of selected electrodes.

30. A method comprising:
storing information identifying neurostimulation therapy programs tested on a patient during a programming session and rating information associated with each of the neurostimulation therapy programs in a memory as part of a session log for the programming session, wherein the rating information for each of the neurostimulation therapy programs comprises at least one numerical rating for a degree of effectiveness of delivery of neurostimulation therapy according to the neurostimulation therapy program in treating symptoms of the patient and at least one numerical rating for a degree of at least one side effect experienced by the patient due to the delivery of neurostimulation therapy according to the neurostimulation therapy program;
displaying a list of the identified neurostimulation therapy programs and associated rating information via a display;
creating a plurality of parameter sets, each of the parameter sets including a plurality of neurostimulation therapy programs;
selecting one of the identified neurostimulation therapy programs from the list based on the rating information; and
including the selected neurostimulation therapy program from the list within at least one of the parameter sets.

31. The method of claim 30, further comprising receiving the rating information from a clinician.

32. The method of claim 30, wherein the rating information includes information relating to performance of the implantable medical device while delivering neurostimulation therapy according to the neurostimulation therapy programs.

33. The method of claim 30, wherein displaying a list comprises displaying a list of the neurostimulation therapy programs ordered according to the rating information.

34. The method of claim 33, wherein the rating information includes information relating to a plurality of metrics for rating the neurostimulation therapy programs.

35. The method of claim 34, wherein displaying a list comprises displaying a list ordered according to selection of one or more of the metrics by a user.

36. The method of claim 34, wherein displaying a list comprises:
calculating an overall rating for each of the neurostimulation therapy programs of the session log based on at least some of the numerical ratings; and
displaying a list of the neurostimulation therapy programs ordered according to the overall ratings.

37. The method of claim 36, wherein calculating an overall rating comprises applying weighting factors to at least some of the numerical ratings.

38. The method of claim 30, wherein the selected neurostimulation therapy program is selected by a user.

39. The method of claim 30, further comprising:
receiving a neurostimulation therapy program selection made by a user from the list; and
storing the selected neurostimulation therapy program as part of a program library within a memory according to a set of hierarchical categories that relate to characteristics of neurostimulation programs.

40. The method of claim 30, wherein selecting one of the identified neurostimulation therapy programs from the list based on the rating information comprises automatically selecting one of the identified neurostimulation therapy programs from the list based on the rating information.

41. A method comprising:
storing information identifying neurostimulation therapy programs tested on a patient during a programming session and rating information associated with each of the neurostimulation therapy programs that comprises at least one numerical rating for effectiveness of delivery of neurostimulation therapy according to the neurostimulation therapy programs in treating symptoms of the patient and at least one numerical rating for at least one side effect experienced by the patient due to the delivery of neurostimulation therapy according to the neurostimulation therapy programs in a memory as part of a session log for the programming session;
displaying a list of the identified neurostimulation therapy programs and associated rating information via a display; and
prompting a user to select at least one of two compared neurostimulation therapy programs for removal from the list.

42. A device comprising:
a display to display information to a user;
a memory to store a session log for a patient that includes information identifying neurostimulation therapy programs tested on the patient during a programming session and rating information associated with each of the neurostimulation therapy programs, wherein the rating information for each of the neurostimulation therapy programs comprises at least one numerical rating for a degree of effectiveness of delivery of neurostimulation therapy according to the neurostimulation therapy programs in treating symptoms of the patient and at least one numerical value for a degree of at least one side effect experienced by the patient due to the delivery of neurostimulation therapy according to the neurostimulation therapy programs;
a processor programmed to display a list of the identified neurostimulation therapy programs and associated rating information via the display, create a plurality of parameter sets, each of the parameter sets including a plurality of neurostimulation therapy programs, select one of the identified neurostimulation therapy programs from the list based on the rating information, and include the selected neurostimulation therapy program from the list within at least one of the parameter sets.

43. The device of claim 42, wherein the rating information includes information relating to performance of an implantable medical device while delivering neurostimulation therapy according to the neurostimulation therapy program.

44. The device of claim 42, wherein the processor displays the list of the neurostimulation therapy programs ordered according to the rating information.

45. The device of claim 44, wherein the rating information includes information relating to a plurality of metrics for rating the neurostimulation therapy programs, and wherein the processor displays the list ordered according to a metric selected by a user.

46. The device of claim 44, wherein the processor calculates an overall rating for each of the neurostimulation therapy programs based on at least some of the numerical ratings, and displays the list ordered according to the overall ratings.

47. The device of claim 44, wherein the processor selects the neurostimulation therapy program from the list by receiving a selection made by a user from the list.

48. The device of claim 42, wherein the processor automatically selects the neurostimulation therapy program for inclusion in at least one of the parameter sets based on the rating information.

49. A non-transitory computer-readable medium comprising instructions that cause a processor to:
store a session log for a patient that includes information identifying neurostimulation therapy programs tested on the patient during a programming session and rating information associated with each of the neurostimulation therapy programs, wherein the rating information for each of the neurostimulation therapy programs comprises at least one numerical rating for a degree of effectiveness of delivery of neurostimulation therapy according to the neurostimulation therapy programs in treating symptoms of the patient and at least one numerical rating for a degree of at least one side effect experienced by the patient due to the delivery of neurostimulation therapy according to the neurostimulation therapy programs in a memory;
display a list of the identified neurostimulation therapy programs and associated rating information via a display;
create a plurality of parameter sets, each of the parameter sets including a plurality of neurostimulation therapy programs;
select one of the identified neurostimulation therapy programs from the list based on the rating information; and
include the selected neurostimulation therapy program from the list within at least one of the parameter sets.

50. The computer-readable medium of claim 49, wherein the instructions cause a processor to display the list of the neurostimulation therapy programs ordered according to the rating information.

51. The computer-readable medium of claim 50, wherein the rating information includes information relating to a plurality of metrics for rating the neurostimulation therapy program, and wherein the instructions cause a processor to display the list ordered according to a metric selected by a user.

52. The computer-readable medium of claim 50, wherein the instructions cause a processor to calculate an overall rating for each of the neurostimulation therapy programs of the session log based on at least some of the numerical ratings, and display the list ordered according to the overall ratings.

53. The computer-readable medium of claim 49, wherein the instructions that cause a processor to select a neurostimulation therapy program from the list comprise instructions that cause a processor to:
receive a neurostimulation therapy program selection made by a user from the list; and
include the selected neurostimulation therapy program within a parameter set.

54. The computer-readable medium of claim 49, wherein the instructions that cause a processor to select a neurostimulation therapy program from the list comprise instructions that cause a processor to automatically select the neurostimulation therapy program based on the rating information.

55. A method comprising:

controlling an implantable medical device to deliver neurostimulation therapy to a patient according to a plurality of neurostimulation therapy programs;

receiving user-inputted rating information relating to effectiveness of delivery of neurostimulation therapy according to each of the plurality of neurostimulation therapy programs, wherein the rating information comprises at least one user-inputted numerical rating for the effectiveness of delivery of neurostimulation therapy according to each of the plurality of neurostimulation therapy programs;

associating each of the plurality of neurostimulation therapy programs with the respective rating information in a memory;

displaying a list of the plurality of neurostimulation therapy programs and the respective rating information; and prompting a user to select at least one of two compared neurostimulation therapy programs for removal from the list.

56. The method of claim 55, and further comprising prompting the user to select at least one of two compared neurostimulation therapy programs for inclusion in a parameter set.

* * * * *